United States Patent
Drake et al.

(10) Patent No.: US 10,792,613 B1
(45) Date of Patent: Oct. 6, 2020

(54) CLEANING DEVICE

(71) Applicant: Oshkosh Corporation, Oshkosh, WI (US)

(72) Inventors: Dan Drake, Oshkosh, WI (US); Don Gray, Oshkosh, WI (US); Glen Brizius, Oshkosh, WI (US); Allen Wood, Oshkosh, WI (US); Jeromie Johnston, Oshkosh, WI (US); Pete Evans, Oshkosh, WI (US)

(73) Assignee: Oshkosh Corporation, Oshkosh, WI (US)

( * ) Notice: Subject to any disclaimer, the term of this patent is extended or adjusted under 35 U.S.C. 154(b) by 0 days.

(21) Appl. No.: 16/373,069

(22) Filed: Apr. 2, 2019

Related U.S. Application Data

(60) Provisional application No. 62/816,587, filed on Mar. 11, 2019.

(51) Int. Cl.
  *B01D 53/88* (2006.01)
  *B01D 53/86* (2006.01)
  *A61L 9/20* (2006.01)

(52) U.S. Cl.
  CPC .............. *B01D 53/885* (2013.01); *A61L 9/20* (2013.01); *B01D 53/86* (2013.01); *B01D 2255/802* (2013.01); *B01D 2259/804* (2013.01)

(58) Field of Classification Search
  None
  See application file for complete search history.

(56) References Cited

U.S. PATENT DOCUMENTS

| | | |
|---|---|---|
| 3,521,459 A | 7/1970 | Rath |
| 5,015,442 A | 5/1991 | Hirai |
| 5,137,697 A | 8/1992 | Lathan et al. |
| 5,221,520 A | 6/1993 | Cornwell |

(Continued)

FOREIGN PATENT DOCUMENTS

| | | |
|---|---|---|
| CA | 2782363 | 7/2011 |
| DE | 100 60 478 | 6/2002 |

(Continued)

OTHER PUBLICATIONS

Partial Search Report Received for Application No. PCT/US2018/064459, Oshkosh Corporation, dated Apr. 3, 2019, 20 pages.

(Continued)

*Primary Examiner* — Jelitza M Perez
(74) *Attorney, Agent, or Firm* — Foley & Lardner LLP

(57) ABSTRACT

A cleaning device includes a housing, an air driver, an ozone generator, and a catalyst. The housing defines an inlet, an outlet, and an internal cavity connecting the inlet to the outlet. The air driver is positioned within the internal cavity. The air driver is configured to draw contaminated air from an external environment into the inlet and through the internal cavity of the housing to facilitate decontaminating the contaminated air and emitting clean air out of the outlet into the external environment. The ozone generator is positioned within the internal cavity. The ozone generator is configured to generate ozone. The catalyst is positioned within the internal cavity. The ozone and/or the catalyst are configured to interact with the contaminated air to produce the clean air.

20 Claims, 18 Drawing Sheets

(56) References Cited

U.S. PATENT DOCUMENTS

| | | |
|---|---|---|
| 5,266,275 A | 11/1993 | Faddis |
| 5,344,622 A | 9/1994 | Faddis et al. |
| 5,681,533 A | 10/1997 | Hiromi |
| 5,833,740 A | 11/1998 | Brais |
| 5,961,919 A | 10/1999 | Tachibana et al. |
| 5,968,214 A | 10/1999 | Nagata et al. |
| 6,066,294 A | 5/2000 | Lin et al. |
| 6,224,828 B1 | 5/2001 | Lin et al. |
| 6,447,731 B1 | 9/2002 | Sun et al. |
| 6,508,982 B1 | 1/2003 | Shoji |
| 6,528,015 B1 | 3/2003 | Lin et al. |
| 6,589,486 B1 | 7/2003 | Spanton |
| 6,620,379 B1 | 9/2003 | Piuk et al. |
| 6,939,336 B2 | 9/2005 | Silfver |
| 6,977,061 B2 | 12/2005 | Lin et al. |
| 7,234,534 B2 | 6/2007 | Froland et al. |
| 7,285,254 B2 | 10/2007 | Lin et al. |
| 7,294,305 B2 | 11/2007 | Lin et al. |
| 7,326,387 B2 | 2/2008 | Arts et al. |
| 7,331,586 B2 | 2/2008 | Trinkner et al. |
| 7,407,633 B2 | 8/2008 | Potember et al. |
| 7,452,410 B2 | 11/2008 | Bergeron et al. |
| 7,468,159 B2 | 12/2008 | Lin et al. |
| 7,504,066 B2 | 3/2009 | Perlov et al. |
| 7,527,603 B2 | 5/2009 | An |
| 7,588,720 B2 | 9/2009 | Turcot et al. |
| 7,615,030 B2 | 11/2009 | Murphy et al. |
| 7,784,554 B2 | 8/2010 | Grady et al. |
| 7,803,316 B2 | 9/2010 | Lin et al. |
| 8,114,358 B2 | 2/2012 | Benedek et al. |
| 8,211,374 B2 | 7/2012 | Hallam |
| 8,277,740 B2 | 10/2012 | Pattee |
| 8,318,084 B2 | 11/2012 | Johnson et al. |
| 8,357,331 B2 | 1/2013 | McVey et al. |
| 8,376,719 B2 | 2/2013 | Grady et al. |
| 8,388,900 B2 | 3/2013 | Benedek et al. |
| 8,529,831 B1* | 9/2013 | Ho ..................... A61L 9/205 422/120 |
| 8,529,832 B2 | 9/2013 | Lee |
| 8,668,883 B2 | 3/2014 | Garner |
| 8,739,892 B2 | 6/2014 | Moore et al. |
| 8,777,889 B2 | 7/2014 | Joshi et al. |
| 8,875,547 B2 | 11/2014 | Suzuki et al. |
| 8,986,520 B2 | 3/2015 | Joshi et al. |
| 9,327,150 B2 | 5/2016 | Moore et al. |
| 9,504,863 B2 | 11/2016 | Moore |
| 9,539,076 B2 | 1/2017 | Almutairi |
| 9,597,536 B1 | 3/2017 | Moore |
| 9,814,915 B2 | 11/2017 | Moore |
| 2002/0074290 A1 | 6/2002 | Jensen |
| 2003/0113246 A1 | 6/2003 | Saitou et al. |
| 2004/0022673 A1 | 2/2004 | Protic |
| 2005/0097870 A1 | 5/2005 | Moshenrose |
| 2005/0163678 A1 | 7/2005 | Clawson et al. |
| 2006/0104858 A1 | 5/2006 | Potember et al. |
| 2007/0039626 A1 | 2/2007 | Schulz |
| 2007/0181000 A1 | 8/2007 | Wilson et al. |
| 2008/0170971 A1 | 7/2008 | Bergeron et al. |
| 2009/0162255 A1 | 6/2009 | Chan et al. |
| 2009/0252654 A1 | 10/2009 | Hsu et al. |
| 2009/0311138 A1 | 12/2009 | Klaptchuk |
| 2010/0003164 A1 | 1/2010 | Bourne et al. |
| 2010/0112677 A1* | 5/2010 | Onishi ..................... A61L 2/202 435/283.1 |
| 2010/0196198 A1 | 8/2010 | Legube |
| 2011/0033346 A1 | 2/2011 | Bohlen et al. |
| 2011/0076192 A1* | 3/2011 | Robitaille ............... A61L 2/202 422/29 |
| 2011/0091354 A1* | 4/2011 | Schwartz ................. A61L 2/22 422/28 |
| 2012/0003126 A1* | 1/2012 | Engelhard ............... A61L 9/205 422/121 |
| 2012/0189490 A1 | 7/2012 | Van Den Bossche et al. |
| 2013/0047857 A1 | 2/2013 | Bohlen |
| 2013/0287626 A1 | 10/2013 | Benedek et al. |
| 2016/0265796 A1 | 9/2016 | Carbone et al. |
| 2017/0246333 A1 | 8/2017 | Carbone et al. |
| 2018/0036446 A1 | 2/2018 | Rice et al. |
| 2018/0064973 A1 | 3/2018 | Moore |
| 2018/0264157 A1* | 9/2018 | Benedek .................. A61L 2/10 |
| 2018/0264160 A1 | 9/2018 | Benedek et al. |
| 2018/0361009 A1 | 12/2018 | Kim et al. |
| 2019/0030195 A1 | 1/2019 | Hatti et al. |
| 2019/0240370 A1 | 8/2019 | Benedek et al. |
| 2019/0240371 A1 | 8/2019 | Benedek et al. |

FOREIGN PATENT DOCUMENTS

| | | |
|---|---|---|
| DE | 20 2017 007 059 U1 | 6/2019 |
| EP | 1 799 330 | 6/2007 |
| EP | 2 651 536 A1 | 10/2013 |
| JP | 02-174987 | 7/1990 |
| JP | 02-174988 | 7/1990 |
| JP | 2000-202493 A | 7/2000 |
| JP | 2000-202793 | 7/2000 |
| JP | 2001-212586 | 8/2001 |
| JP | 2001-219181 | 8/2001 |
| JP | 2004-019957 | 1/2004 |
| WO | WO-2008/082452 A1 | 7/2008 |
| WO | WO-2011/038487 A1 | 4/2011 |
| WO | WO-2011/142596 | 11/2011 |
| WO | WO-2013/110782 A1 | 8/2013 |
| WO | WO-2018/160412 | 9/2018 |
| WO | WO-2018/167528 A1 | 9/2018 |
| WO | WO-2019/147501 | 8/2019 |
| WO | WO-2019/152996 | 8/2019 |
| WO | WO-2019/240371 | 12/2019 |

OTHER PUBLICATIONS

Scent Crusher: Ozone Hunter's Closet, obtained from website: https://scentcrusher.com/hunters-closet/, 3 pps.

Scent Crusher: Ozone Go, obtained from website: https://scentcrusher.com/ozone-go/, 8 pps.

International Search Report and Written Opinion on PCT/US2018/064459, dated May 24, 2019, 24 pages.

Invitation to Pay Additional Fees and Partial Int'l Search Report regarding Appl. No. PCT PCT/US2020/021874 dated Jun. 8, 2020, 19 pps.

* cited by examiner

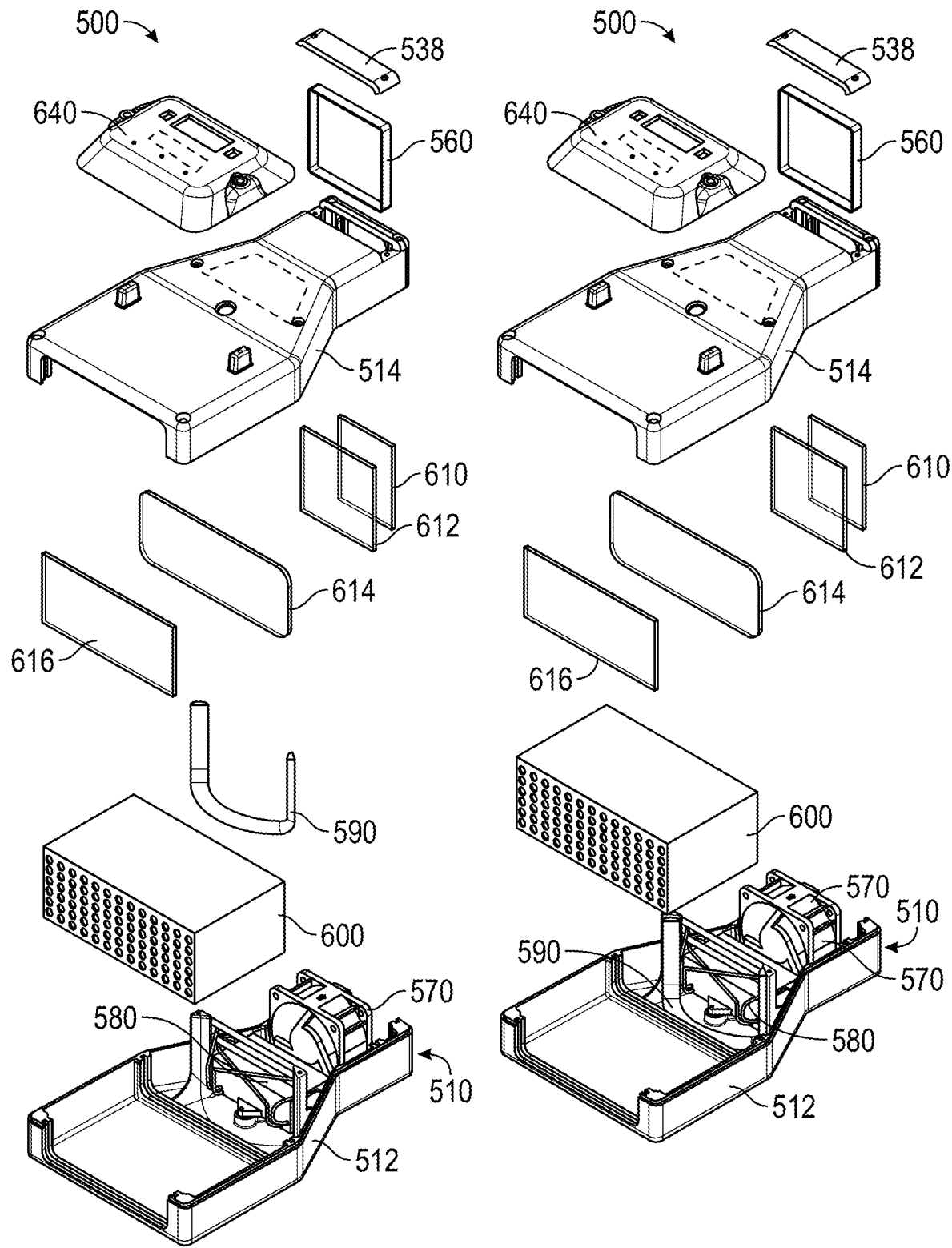

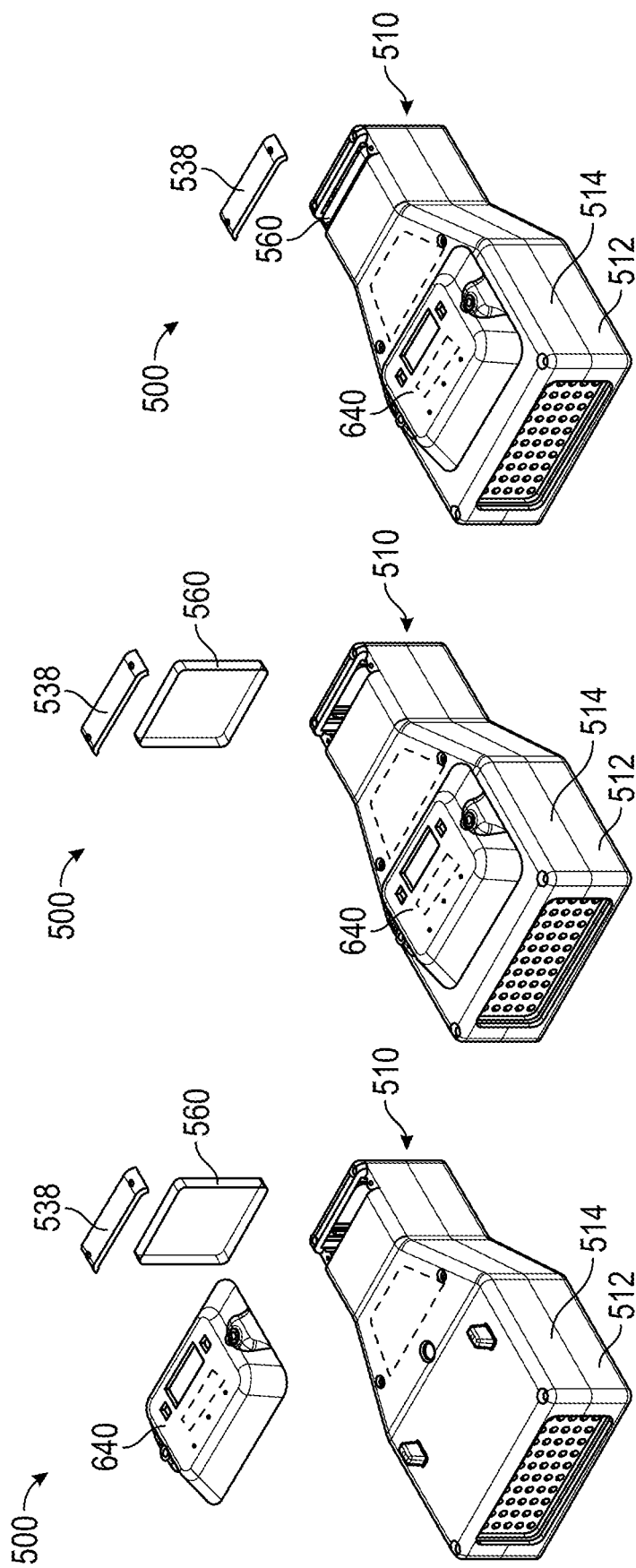

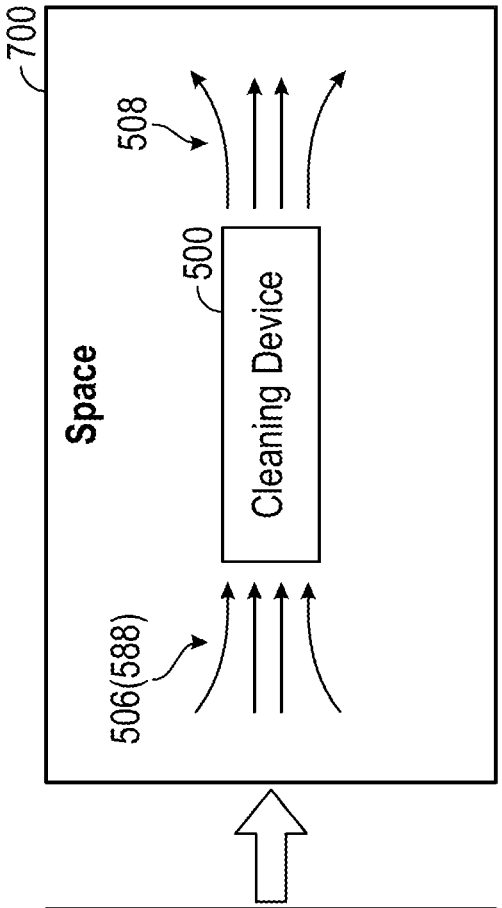
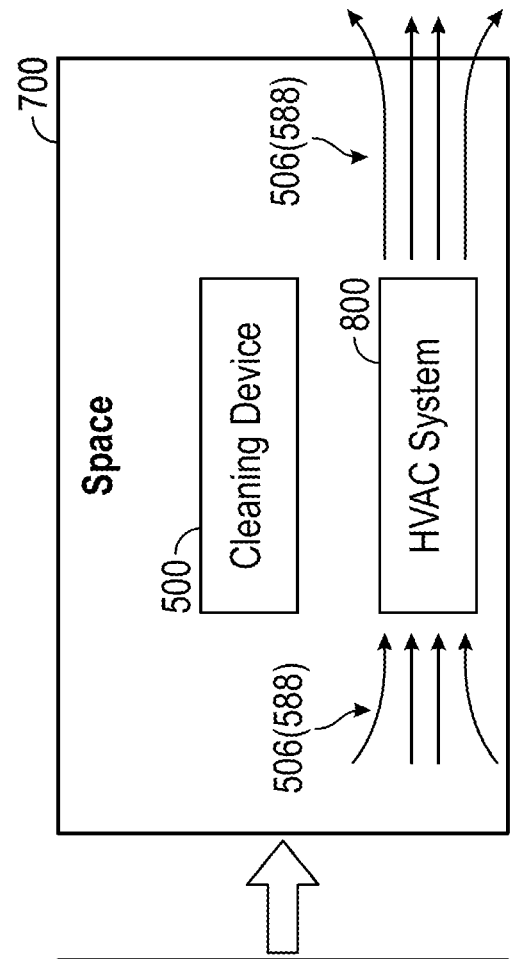
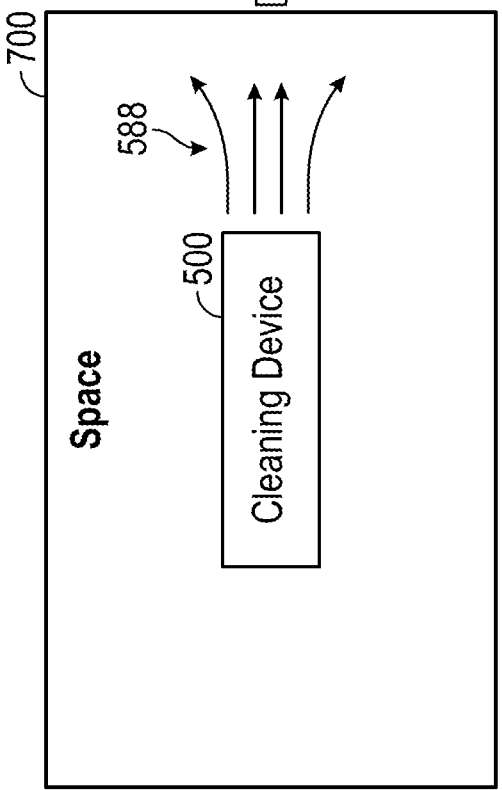
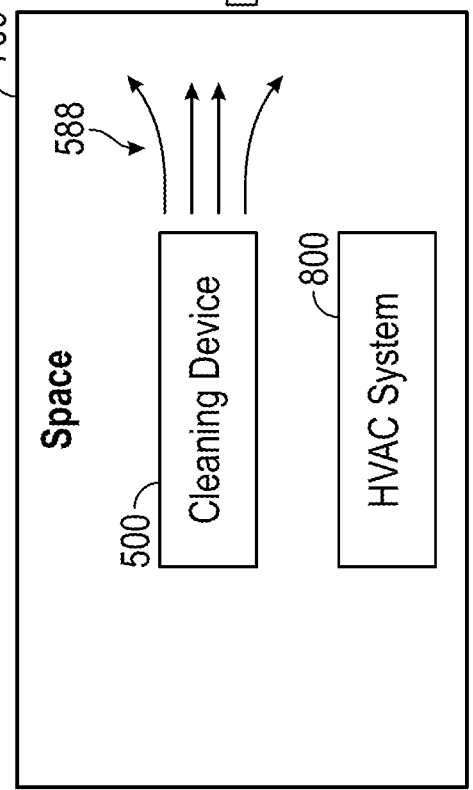

CLEANING DEVICE

CROSS-REFERENCE TO RELATED PATENT APPLICATIONS

This application claims the benefit of U.S. Provisional Patent Application No. 62/816,587, filed Mar. 11, 2019, which is incorporated herein by reference in its entirety.

BACKGROUND

Firefighters are at a higher risk of health ailments (e.g., cancer) than the general public. This has been attributed to carcinogens released from burning materials at the scene of a fire. Such carcinogens can contaminate the interior cabs of vehicles and the interior of buildings and cause health risks to the occupants thereof. Further, pathogens within enclosed spaces (e.g., hospitals, restrooms, vehicles, etc.) can cause health risks to the occupants thereof.

SUMMARY

One embodiment relates to a cleaning device. The cleaning device includes a housing, an air driver, an ozone generator, and a catalyst. The housing defines an inlet, an outlet, and an internal cavity connecting the inlet to the outlet. The air driver is positioned within the internal cavity. The air driver is configured to draw contaminated air from an external environment into the inlet and through the internal cavity of the housing to facilitate decontaminating the contaminated air and emitting clean air out of the outlet into the external environment. The ozone generator is positioned within the internal cavity. The ozone generator is configured to generate ozone. The catalyst is positioned within the internal cavity. The ozone and/or the catalyst are configured to interact with the contaminated air to produce the clean air.

Another embodiment relates to vehicle. The vehicle includes a chassis, a cab coupled to the chassis, and a cleaning device. The cab defines an interior space. The cleaning device is positioned within the cab. The cleaning device includes an ozone generator configured to generate ozone to interact with contaminates within the interior space to neutralize the contaminates.

Still another embodiment relates to a cleaning device. The cleaning device includes a housing, a filter, an air driver, an ozone generator, and ultraviolet light source, a photocatalyst, and a catalyst. The housing defines an inlet, an outlet, and an internal cavity connecting the inlet to the outlet. The filter is positioned within the internal cavity, proximate the inlet. The air driver is positioned within the internal cavity, downstream of the filter. The air driver is configured to drive air through the internal cavity. The ozone generator is positioned within the internal cavity, downstream of the air driver. The ozone generator is configured to generate ozone. The ultraviolet light source is positioned within the internal cavity, downstream of the ozone generator. The ultraviolet light source is configured to emit ultraviolet light. The photocatalyst is positioned within the internal cavity, downstream of the ultraviolet light source such that a gap is defined between the ultraviolet light source and the photocatalyst. The ultraviolet light is configured to activate the photocatalyst. The catalyst is positioned within the internal cavity, downstream of the photocatalyst, proximate the outlet.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

BRIEF DESCRIPTION OF THE DRAWINGS

FIGS. 14-22 are various exploded views depicting a method of assembling the cleaning device of FIG. 4, according to an exemplary embodiment.

FIGS. 27A and 27B are various schematic views of a cleaning device disposed within a space and operable in a second mode, according to an exemplary embodiment.

FIGS. 28A and 28B are various schematic views of a cleaning device disposed within a space and operable in a second mode in combination with a HVAC system, according to an exemplary embodiment.

DETAILED DESCRIPTION

Figure 1:
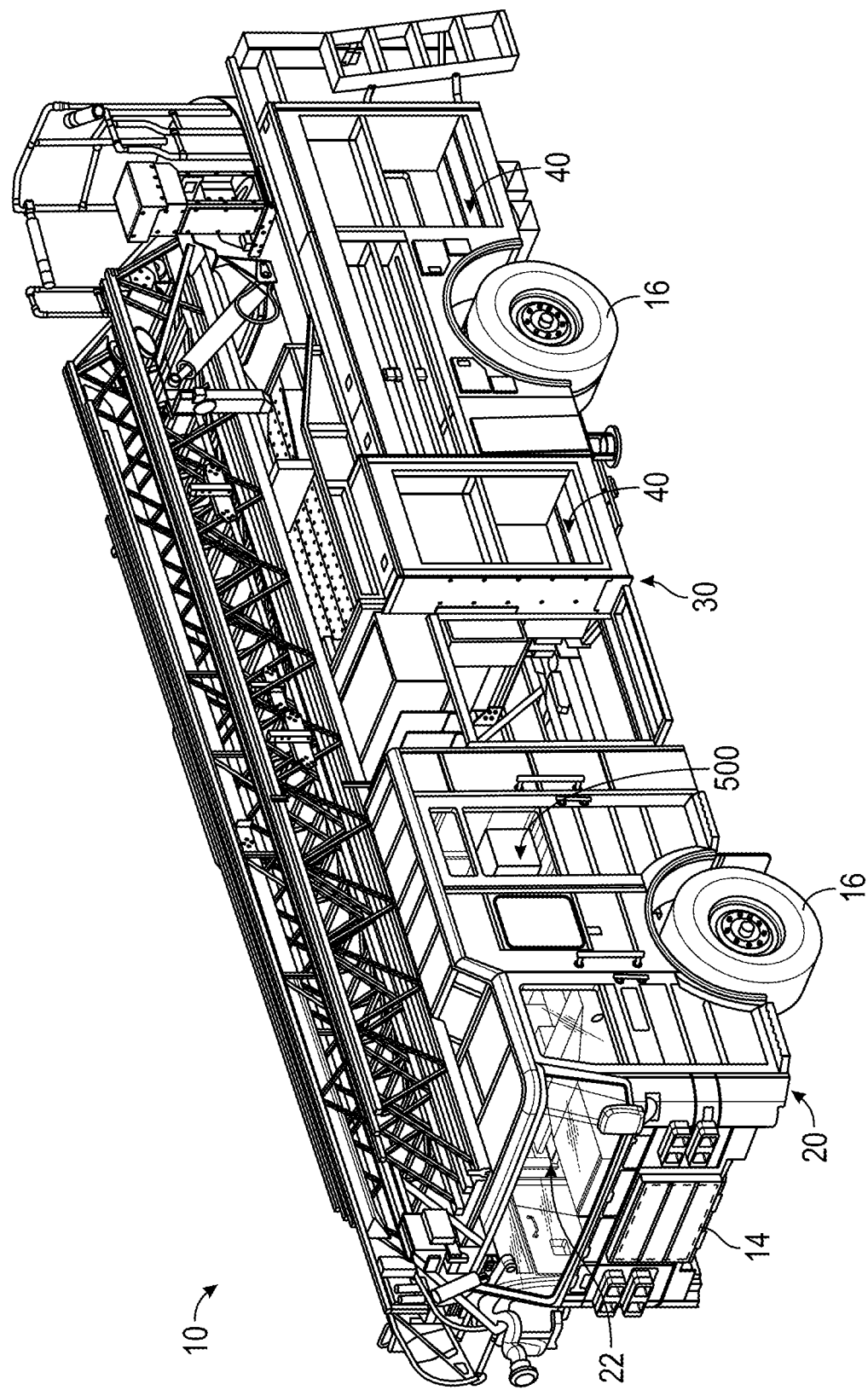
FIG. 1 is a perspective view of a firefighting vehicle, according to an exemplary embodiment.

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

According to an exemplary embodiment, a cleaning device is configured to facilitate decontaminating at least one of a space (e.g., an interior of a vehicle, a room, etc.) and/or equipment/objects within the space (e.g., gear, seats, dashes, interfaces, upholstery, etc.). In one embodiment, the cleaning device is a standalone unit having a housing that may be positioned inside of a cab of a vehicle, inside of a compartment of a vehicle, inside of a building, etc. In another embodiment, the cleaning device is integrated into a cab of a vehicle, a compartment of the vehicle, and/or a building. The cleaning device may facilitate decontaminating such spaces and/or equipment/objects to neutralize carcinogens, pathogens, and/or other harmful contaminants that can build up over time.

First-responders are often exposed to hazardous situations during the course of their duties. One of the most dangerous situations arises when personnel are exposed to hazardous chemicals. Trace amounts of these chemicals may coat the surface of clothing and protective gear of the first-responders, as well as contaminate the interior of vehicles, and given their toxicity, can be harmful. Compounds such as benzene, benzopyrene, butadiene, carbon monoxide, formaldehyde, dibenzanthracene, trichloroethylene, tetrachloroethylene, and polychlorinated biphenyls are all present in the environment either from their past use in industry (e.g., in cleaning products, lubricants, etc.) or as decomposition products from other compounds.

According to an exemplary embodiment, the cleaning device of the present disclosure is configured to implement a decontamination process that uses ozone, moist/humidified air, ultraviolet light, and/or one or more catalysts to break down such dangerous compounds, such as carcinogens, into harmless carbon dioxide, water, and/or chloride salts. Ozone is a pale blue gas that is generated naturally in the upper atmosphere, but can also be generated using specifically designed devices. There really is no practical way to store Ozone such that it must be generated as needed (i.e., because of its high reactivity). Regular oxygen that we breathe consists of two oxygen atoms bound together, and is represented as $O_2$. Ozone is related to oxygen, but it has three oxygen atoms bound together, and is represented as $O_3$. Ozone can be visualized as a regular oxygen molecule that has a very energetic, active, and excited companion, a single oxygen atom. Atomic oxygen ($O_1$) does not like to be alone and tries to use its energy to find a partner to bond or interact with. As a result, atomic oxygen will react with just about anything on contact. The atomic oxygen within ozone cannot be stable until it moves away from the 02 molecule and forms a molecule with something else. If the atomic oxygen cannot find anything, it will eventually react with another oxygen atom that is in the same situation and they will stabilize each other, forming regular oxygen ($O_2$). Such behavior makes ozone a very powerful oxidant.

Further, the cleaning device of the present disclosure may be configured to neutralize various pathogens. By way of example, the ozone generated by the cleaning device may attack the cell walls of pathogens (e.g., bacteria, viruses, microorganisms, etc.). Such pathogens may include influenza, MRSA, staph, Cdiff, etc. Once the cell walls of the pathogens are compromised, the cells die and the pathogen is eliminated, leaving oxygen, carbon dioxide, water, and sodium chloride. Accordingly, the cleaning device may be configured to implement a decontamination process to treat and break down harmful pollutants (e.g., carcinogens, pathogens, etc.) into carbon dioxide, water, and/or sodium chloride (i.e., table salt) using generated ozone, moisture, ultraviolet light, and/or one or more catalysts.

Figure 2:
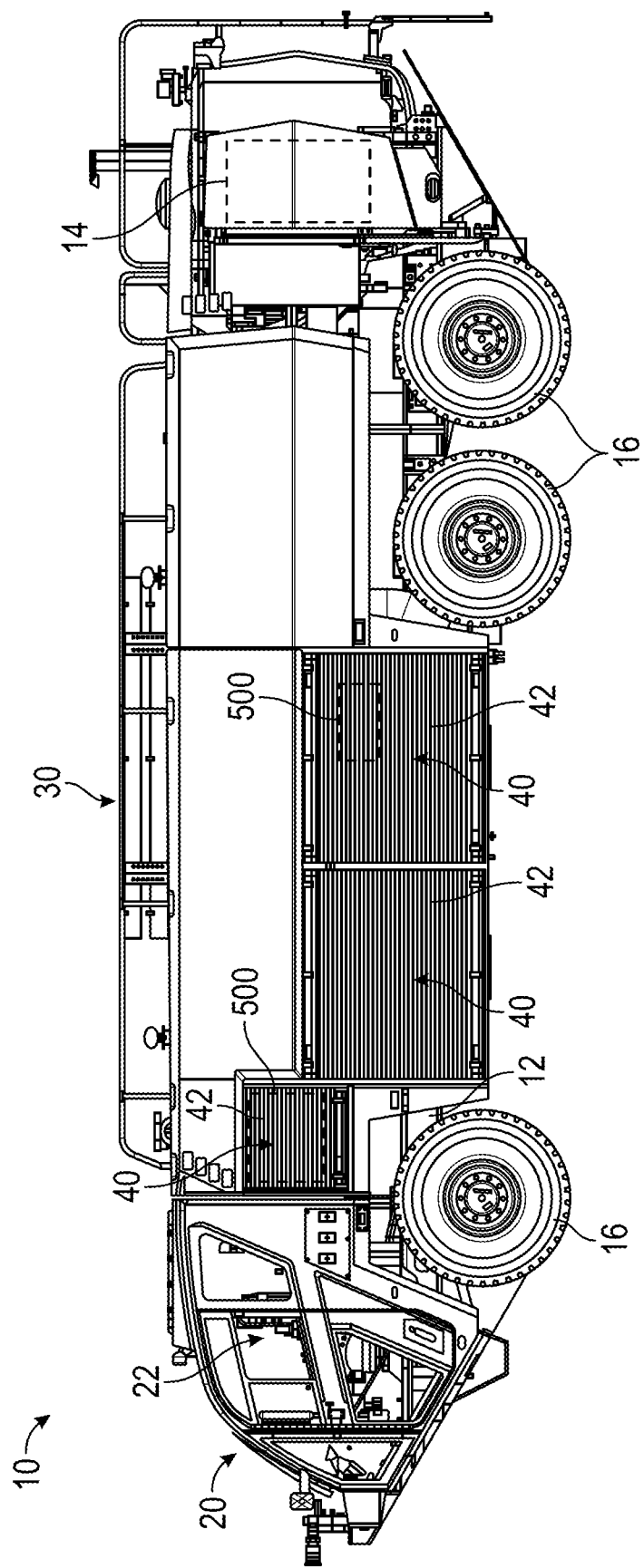
FIG. 2 is a perspective view of an airport firefighting vehicle, according to an exemplary embodiment.

According to the exemplary embodiment shown in FIGS. 1 and 2, a vehicle, shown as vehicle 10, includes a cleaning system, shown as cleaning device 500. The cleaning device 500 may be configured neutralize organic carcinogens, pathogens, pollutants, and/or other contaminates. In one embodiment, the cleaning device 500 is a standalone unit that may be positioned within the vehicle 10, in a firehouse or station, and/or at any other suitable space the cleaning device 500 may fit. In another embodiment, the cleaning device 500 is integrated into the vehicle 10 (e.g., within a cab thereof; within the heating, ventilation, and air conditioning ("HVAC") system thereof; within a storage compartment thereof; etc.). The cleaning device 500 may be capable of cleaning, disinfecting, and/or decontaminating loose items (e.g., firefighting gear, etc.), an interior of the vehicle 10, air within the vehicle 10, and/or other suitable spaces or components.

According to the exemplary embodiment shown in FIG. 1, the vehicle 10 is configured as a single rear axle quint fire truck. In other embodiments, the vehicle 10 is configured as a tandem rear axles quint fire truck. In still other embodiments, the vehicle 10 is configured as another type of fire apparatus such as a tiller fire truck, an aerial platform fire truck, a mid-mount fire truck, etc. According to the exemplary embodiment shown in FIG. 2, the vehicle 10 is configured as an airport rescue firefighting ("ARFF") truck. In other embodiments, the vehicle 10 is still another type of fire apparatus. In still other embodiments, the vehicle 10 is another type of vehicle (e.g., a refuse vehicle, a boom truck, a plow truck, a military vehicle, an ambulance, a police vehicle, etc.).

As shown in FIGS. 1 and 2, the vehicle 10 includes a chassis, shown as frame 12; a front cabin, shown as cab 20, coupled to the frame 12 (e.g., at a front end thereof, etc.) and defining an interior, shown as interior 22; and a rear assembly, shown as rear assembly 30, coupled to the frame 12 (e.g., at a rear end thereof, etc.). The cab 20 may include various components to facilitate operation of the vehicle 10 by an operator (e.g., a seat, a steering wheel, hydraulic controls, a user interface, switches, buttons, dials, etc.). The vehicle 10 includes a prime mover, shown as engine 14, coupled to the frame 12. As shown in FIG. 1, the engine 14 is positioned beneath the cab 20. As shown in FIG. 2, the engine 14 is positioned within the rear assembly 30 at the rear of the vehicle 10. As shown in FIGS. 1 and 2, the vehicle 10 includes a plurality of tractive elements, shown as wheel and tire assemblies 16. In other embodiments, the tractive elements include track elements. According to an exemplary embodiment, the engine 14 is configured to provide power to the wheel and tire assemblies 16 and/or to other systems of the vehicle 10 (e.g., a pneumatic system, a hydraulic system, etc.). The engine 14 may be configured to utilize one or more of a variety of fuels (e.g., gasoline, diesel, bio-diesel, ethanol, natural gas, etc.), according to various exemplary embodiments. According to an alternative embodiment, the engine 14 additionally or alternatively includes one or more electric motors coupled to the frame 12 (e.g., a hybrid vehicle, an electric vehicle, etc.). The electric motors may consume electrical power from an on-board storage device (e.g., batteries, ultra-capacitors, etc.), from an on-board generator (e.g., an internal combustion engine genset, etc.), and/or from an external power source (e.g., overhead power lines, etc.) and provide power to the systems of the vehicle 10.

As shown in FIGS. 1 and 2, the rear assembly 30 includes various compartments, shown as compartments 40. As shown in FIG. 2, the compartments 40 include doors, shown as doors 42. The doors 42 of the compartments 40 may be selectively opened to access an interior of the compartments 40. The interior of the compartments may store components of the vehicle 10, tools (e.g., firefighting tools, etc.), and/or gear (e.g., firefighting gear, etc.).

As shown in FIG. 1, the cleaning device 500 is disposed within the interior 22 of the cab 20 of the vehicle 10. In such an embodiment, the cleaning device 500 may be a standalone unit removable from the cab 20 and/or an integrated system within the cab 20. As shown in FIG. 2, the cleaning device 500 is disposed in one or more of the compartments 40 of the vehicle 10. In such an embodiment, the cleaning device 500 may be a standalone unit removable from the one or more compartments 40 and/or an integrated system within the one or more compartments 40. In embodiments where the cleaning device 500 is a standalone unit, the cleaning device 500 may be positioned at any suitable location (e.g., within a firehouse, a fire station, a hospital room, a doctor's office, etc.).

Figure 3:
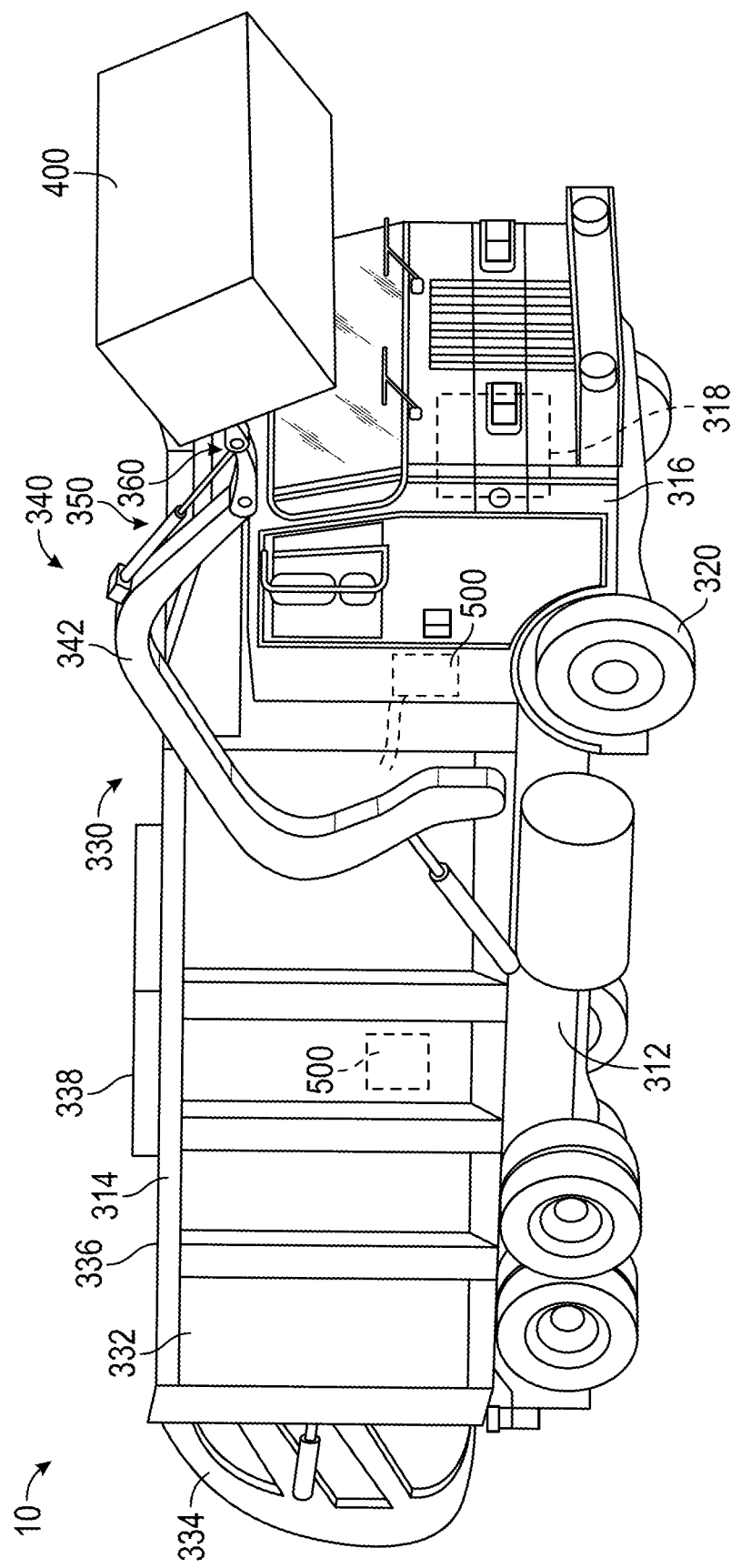
FIG. 3 is a perspective view of a refuse vehicle, according to an exemplary embodiment.

According to the exemplary embodiment shown in FIG. 3, the vehicle 10 is configured as a front-loading refuse truck (e.g., a garbage truck, a waste collection truck, a sanitation truck, etc.). In other embodiments, the vehicle 10 is configured as a side-loading refuse truck or a rear-loading refuse truck. As shown in FIG. 3, the vehicle 10 includes a chassis, shown as frame 312; a body assembly, shown as body 314, coupled to the frame 312 (e.g., at a rear end thereof, etc.); and a cab, shown as cab 316, coupled to the frame 312 (e.g., at a front end thereof, etc.). The cab 316 may include various components to facilitate operation of the vehicle 10 by an operator (e.g., a seat, a steering wheel, hydraulic controls, a user interface, switches, buttons, dials, etc.). As shown in FIG. 3, the vehicle 10 includes a prime mover, shown as engine 318, coupled to the frame 312 at a position beneath the cab 316. The engine 318 is configured to provide power to a plurality of tractive elements, shown as wheels 320, and/or to other systems of the vehicle 10 (e.g., a pneumatic system, a hydraulic system, etc.). The engine 318 may be configured to utilize one or more of a variety of fuels (e.g., gasoline, diesel, bio-diesel, ethanol, natural gas, etc.), according to various exemplary embodiments. According to an alternative embodiment, the engine 318 additionally or alternatively includes one or more electric motors coupled to the frame 312 (e.g., a hybrid refuse vehicle, an electric refuse vehicle, etc.). The electric motors may consume electrical power from an on-board storage device (e.g., batteries, ultra-capacitors, etc.), from an on-board generator (e.g., an internal combustion engine, etc.), and/or from an external power source (e.g., overhead power lines, etc.) and provide power to the systems of the vehicle 10.

According to an exemplary embodiment, the vehicle 10 is configured to transport refuse from various waste receptacles within a municipality to a storage and/or processing facility (e.g., a landfill, an incineration facility, a recycling facility, etc.). As shown in FIG. 3, the body 314 includes a plurality of panels, shown as panels 332, a tailgate 334, and a cover 336. The panels 332, the tailgate 334, and the cover 336 define a collection chamber (e.g., hopper, etc.), shown as refuse compartment 330. Loose refuse may be placed into the refuse compartment 330 where it may thereafter be compacted. The refuse compartment 330 may provide temporary storage for refuse during transport to a waste disposal site and/or a recycling facility. In some embodiments, at least a portion of the body 314 and the refuse compartment 330 extend in front of the cab 316. According to the embodiment shown in FIG. 3, the body 314 and the refuse compartment 330 are positioned behind the cab 316. In some embodiments, the refuse compartment 330 includes a hopper volume and a storage volume. Refuse may be initially loaded into the hopper volume and thereafter compacted into the storage volume. According to an exemplary embodiment, the hopper volume is positioned between the storage volume and the cab 316 (i.e., refuse is loaded into a position of the refuse compartment 330 behind the cab 316 and stored in a position further toward the rear of the refuse compartment 330). In other embodiments, the storage volume is positioned between the hopper volume and the cab 316 (e.g., a rear-loading refuse vehicle, etc.).

As shown in FIG. 3, the vehicle 10 includes a lift mechanism/system (e.g., a front-loading lift assembly, etc.), shown as lift assembly 340. The lift assembly 340 includes a pair of arms, shown as lift arms 342, coupled to the frame 312 and/or the body 314 on either side of the vehicle 10 such that the lift arms 342 extend forward of the cab 316 (e.g., a front-loading refuse vehicle, etc.). In other embodiments, the lift assembly 340 extends rearward of the body 314 (e.g., a rear-loading refuse vehicle, etc.). In still other embodiments, the lift assembly 340 extends from a side of the body 314 (e.g., a side-loading refuse vehicle, etc.). The lift arms 342 may be rotatably coupled to frame 312 with a pivot (e.g., a lug, a shaft, etc.). As shown in FIG. 3, the lift assembly 340 includes first actuators, shown as lift arm actuators 344 (e.g., hydraulic cylinders, etc.), coupled to the frame 312 and the lift arms 342. The lift arm actuators 344 are positioned such that extension and retraction thereof rotates the lift arms 342 about an axis extending through the pivot, according to an exemplary embodiment.

As shown in FIG. 3, the vehicle 10 includes forks, shown as lift forks 360, coupled to the lift arms 342 of the lift assembly 340. The lift forks 360 are configured to engage with a container, shown as refuse container 400, to selectively and releasably secure the refuse container 400 to the lift assembly 340. As shown in FIG. 3, the lift arms 342 are rotated by the lift arm actuators 344 to lift the refuse container 400 over the cab 316. The lift assembly 340 includes second actuators, shown as articulation actuators 350 (e.g., hydraulic cylinders, etc.). According to an exemplary embodiment, the articulation actuators 350 are positioned to articulate the lift forks 360. Such articulation may assist in tipping refuse out of the refuse container 400 and into the hopper volume of the refuse compartment 330 through an opening in the cover 336. The lift arm actuators 344 may thereafter rotate the lift arms 342 to return the empty refuse container 400 to the ground. According to an exemplary embodiment, a door, shown as top door 338, is movably coupled along the cover 336 to seal the opening thereby preventing refuse from escaping the refuse compartment 330 (e.g., due to wind, bumps in the road, etc.).

As shown in FIG. 3, the vehicle 10 includes the cleaning device 500. In one embodiment, the cleaning device 500 is disposed within the cab 316. In such an embodiment, the cleaning device 500 may be (i) integrated directly into the interior of the cab 316 such that the cleaning device 500 is configured to facilitate decontaminating and neutralizing contaminants disposed within the interior of the cab 316. In some embodiments, a second cleaning device 500 is additionally or alternatively disposed within the refuse compartment 330. In such an embodiment, the second cleaning device 500 may be integrated directly into the refuse compartment 330.

While the cleaning device 500 described herein is mainly described in the context of firefighting and refuse applications, it should be understood that the cleaning device 500 may be used in various different applications. By way of example, the cleaning device 500 may be implemented in various different types of vehicles to facilitate neutralizing toxins (e.g., carcinogens, pathogens, pollutants, contaminants, etc.) within cabs of the vehicles, within compartments of the vehicles, and/or on gear stored within the vehicle. For example, the cleaning device 500 may be used with fire trucks, refuse vehicles, concrete mixer vehicles, ambulances, tanks, submarines, space stations, spacecrafts, aircrafts, military vehicles, police vehicles, buses, trains, trams, subways, semi-trucks, RVs, campers, passenger vehicles (e.g., personal vehicles, taxis, rideshare vehicles, rental vehicles, etc.), and/or still other types of vehicles that may encounter carcinogens, pathogens, and/or other pollutants or contaminants during use. By way of another example, the cleaning device 500 may be implemented in various different types of non-vehicle spaces such as fire houses, military barracks, locker rooms, dorm rooms, restrooms, portable restrooms (e.g., a "porta potty," etc.), hotel rooms, nursing homes, hospitals (e.g., patient rooms, surgical rooms, waiting rooms, etc.), doctor's offices, schools, corporate offices, residential buildings (e.g., houses, condos, apartments, etc.), industrial manufacturing facilities (e.g., chemical manufacturing plants, etc.), and/or still other types of spaces that may encounter carcinogens, pathogens, and/or other pollutants or contaminants during use thereof. By way of still another example, the cleaning device 500 may be integrated directly into gear such as military gear, bomb suits, hazmat suits, fire suits, space suits, helmets, gas masks, and/or other gear that may be used in spaces where the wearer may encounter carcinogens, pathogens, and/or other pollutants or contaminants.

According to the exemplary embodiment shown in FIGS. 4-30, the cleaning device 500 is configured to cycle air from an enclosed space, room, or chamber, within which the cleaning device 500 is positioned, through the cleaning device 500 to clean the air. Accordingly, the cleaning device 500 may be (i) integrated into a vehicle, a space, a room, or a chamber or (ii) a retrofit solution selectively positionable within a vehicle, a space, a room, or a chamber to facilitate decontaminating air and/or components within the vehicle, the space, the room, or the chamber within which the cleaning device 500 is positioned.

Figure 30:
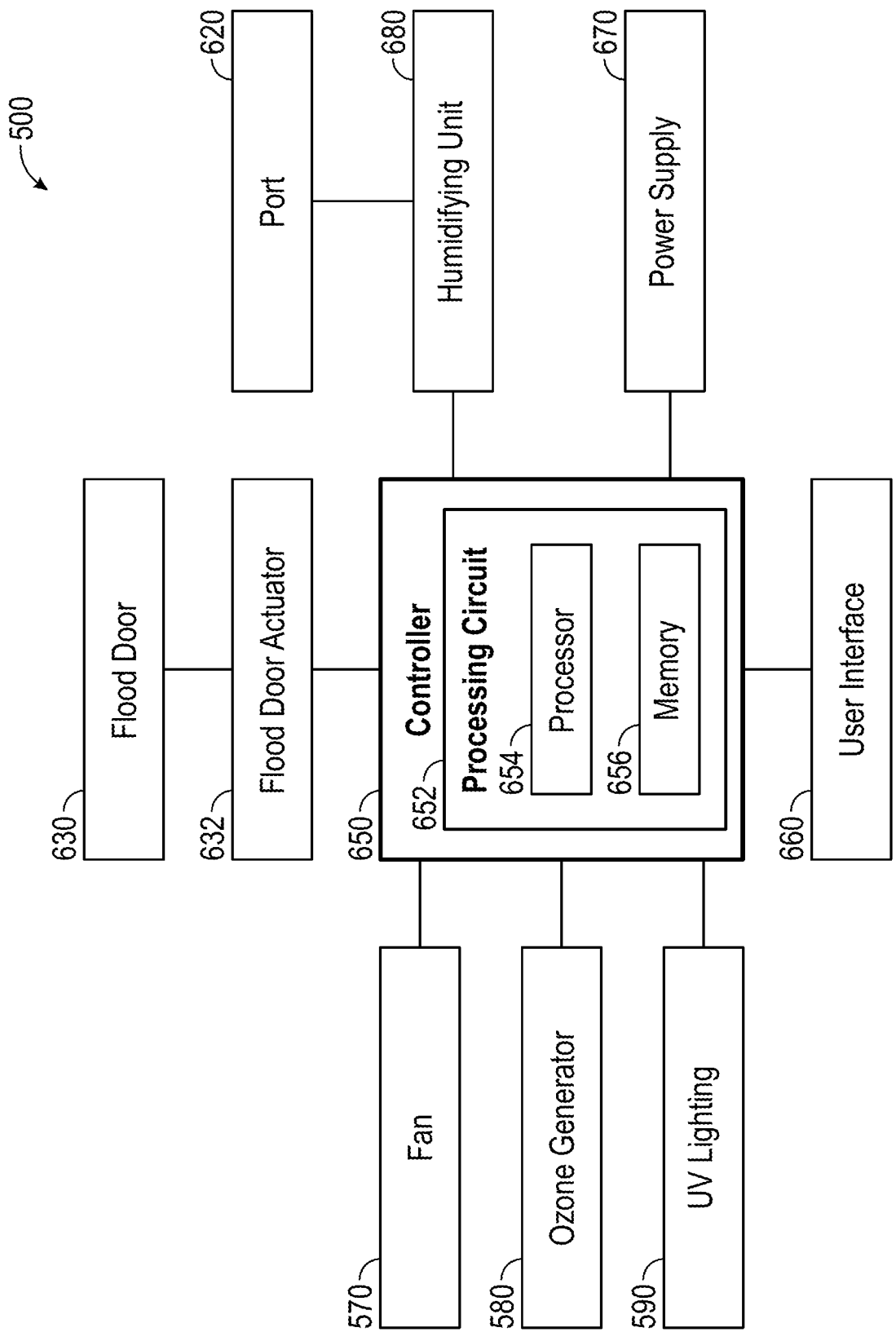
FIG. 30 is a schematic block diagram of the cleaning device of FIGS. 4-29B, according to an exemplary embodiment.

As shown in FIGS. 4-24 and 30, the cleaning device 500 includes a casing, shown as housing 510; a filter, shown as inlet filter 560; an air driver device (e.g., a blower, etc.), shown as fan 570; a generator, shown as ozone generator 580; a light source, shown as UV lighting 590; a first catalyst, shown as catalyst 600; a first screen, shown as filter inlet screen 610; a second screen, shown as filter outlet screen 612; a third screen, shown as catalyst inlet screen 614; a fourth screen, shown as catalyst outlet screen 616; a control assembly, shown as controller housing 640; a control system, shown as controller 650; and a user input/output device, shown as user interface 660. In some embodiments, as shown in FIG. 30, the cleaning device 500 includes or is coupled to a power source, shown as power supply 670, and/or a humidifier or moisture source, shown as humidifying unit 680. In other embodiments, the cleaning device 500 includes additional or fewer components. By way of example, the cleaning device 500 may not include one or more of the fan 570, the ozone generator 580, the UV lighting 590, and the humidifying unit 680. All such variations are described in greater detail herein.

As shown in FIGS. 4-11, 23, and 24, the cleaning device 500 has (i) a first end, shown as inlet end 502, that receives an inlet fluid flow, shown as contaminated air 506, from an external environment (e.g., a space, chamber, compartment, etc. within which the cleaning device 500 is positioned) that interacts with various components of the cleaning device 500 (e.g., the inlet filter 560, the ozone generator 580, the UV lighting 590, the catalyst inlet screen 614, the catalyst 600, etc.) and (ii) an opposing second end, shown as outlet end 504, that emits an outlet fluid flow, shown as clean air 508, into the external environment. According to an exemplary embodiment, the cleaning device 500 is configured to be positioned in spaces that contain carcinogens, pathogens, pollutants, and/or still other contaminants.

Figure 4:
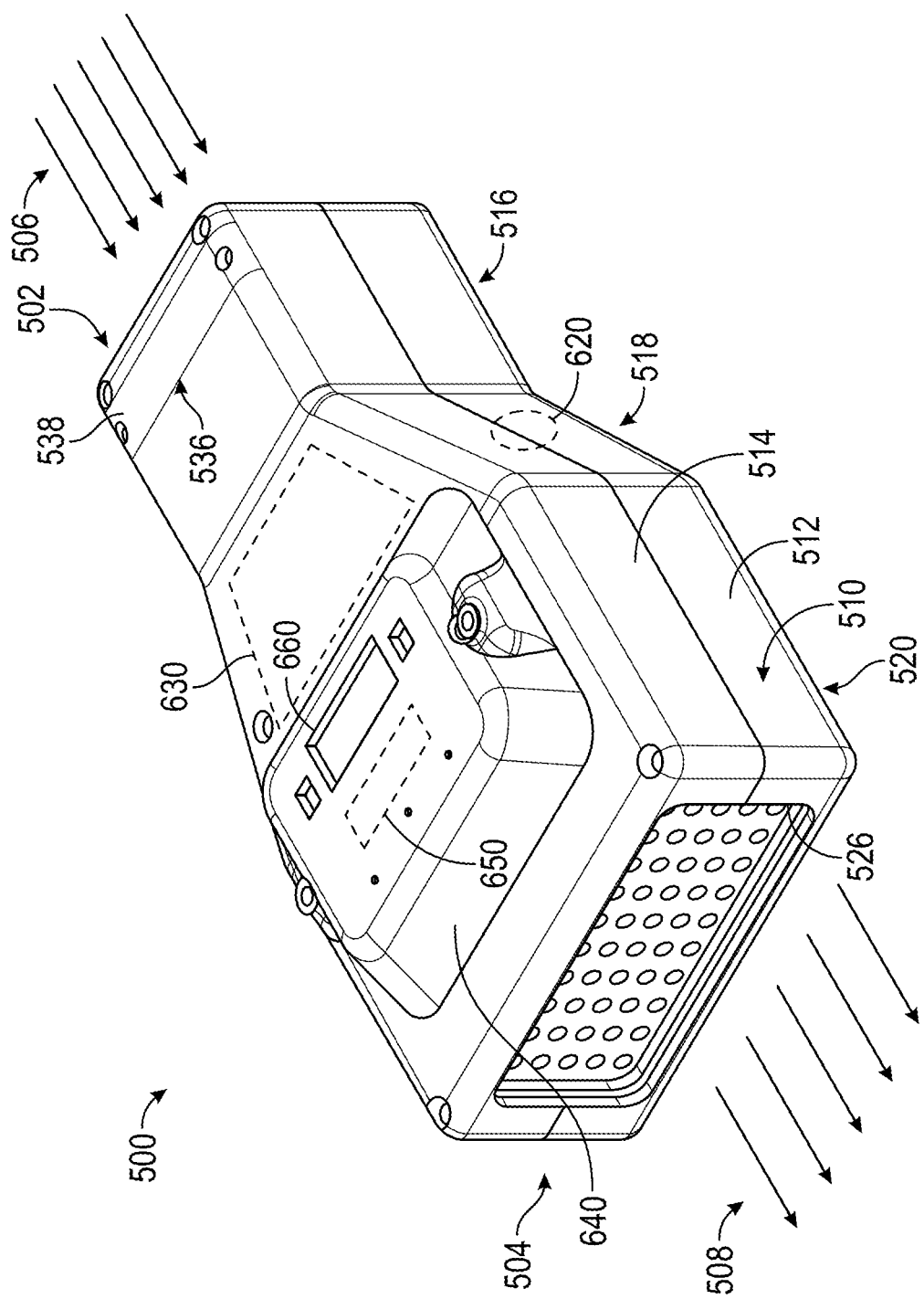
FIG. 4 is a rear perspective view of a cleaning device, according to an exemplary embodiment.
Figure 5:
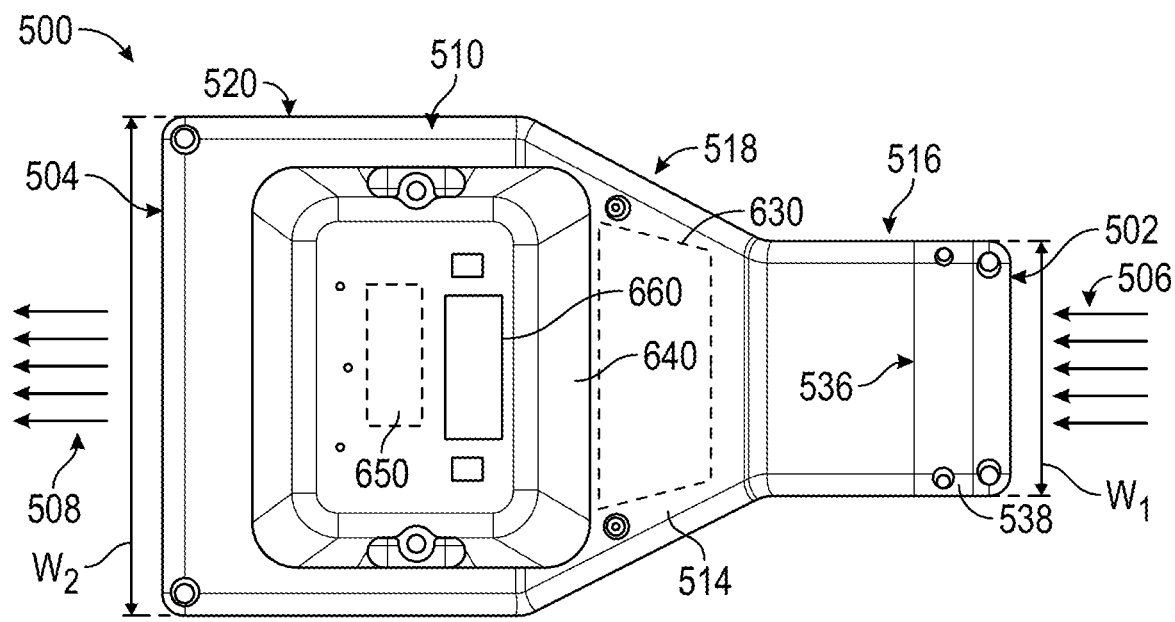
FIG. 5 is a top view of the cleaning device of FIG. 4, according to an exemplary embodiment.
Figure 6:
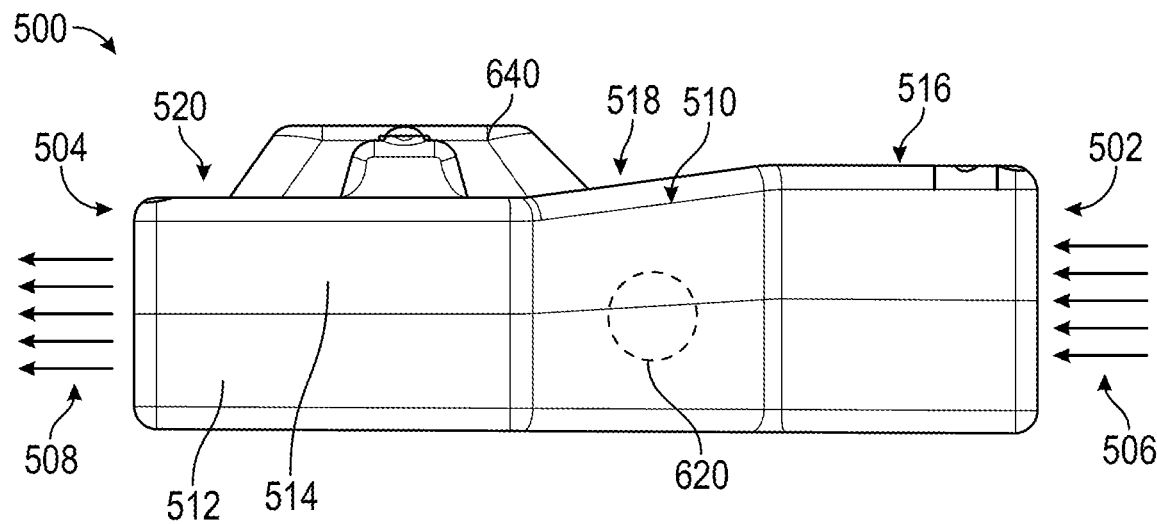
FIG. 6 is a side view of the cleaning device of FIG. 4, according to an exemplary embodiment

As shown in FIGS. 4-11 and 14-24, the housing 510 includes a first portion, shown as base 512, and a second portion, shown a top 514, that selectively couple together (e.g., via fasteners, adhesive, snap fit, etc.). As shown in FIGS. 4-11, the base 512 and the top 514 of the housing 510 cooperatively define a first chamber, shown as inlet chamber 516, a second chamber, shown as ozone chamber 518, and a third chamber, shown as catalyst chamber 520, that cooperatively define an internal cavity of the housing 510, shown as interior cavity 524. As shown in FIG. 5, the inlet chamber 516 has a first width $w_1$ and the catalyst chamber 520 has a second width $w_2$. According to the exemplary embodiment shown in FIG. 5, the first width $w_1$ of the inlet chamber 516 is smaller than the second width $w_2$ of the catalyst chamber 520 with the ozone chamber 518 extending linearly between and connecting the inlet chamber 516 and the catalyst chamber 520. In other embodiments, the ozone chamber 518 extends non-linearly (i.e., has a curved profile) between the inlet chamber 516 and the catalyst chamber 520 (see, e.g., FIGS. 23 and 24). In still other embodiments, the first width $w_1$ of the inlet chamber 516 is larger than the second width $w_2$ of the catalyst chamber 520. In yet other embodiments, the inlet chamber 516, the ozone chamber 518, and the catalyst chamber 520 have the same width (e.g., the housing 510 is a rectangular prism, etc.).

In various embodiments, the first width $w_1$ is at most 8 inches (e.g., 8 inches, 6 inches, 4 inches, 3 inches, 2 inches, etc.), the second width $w_2$ is at most 12 inches (e.g., 12 inches, 10 inches, 8 inches, 6 inches, etc.), and the overall length of the cleaning device 500 is at most 24 inches (e.g., 24 inches, 18 inches, 12 inches, 10 inches, 9 inches, 8 inches, etc.). Such a sized cleaning device 500 may be capable of cleaning the interior of a vehicle (e.g., the interior 22 of the cab 20, etc.), a cabinet, a storage closet, a small room, and/or similarly sized spaces or compartments. According to the exemplary embodiment shown in FIG. 4, the first width $w_1$ is about 2.35 inches, the second width $w_2$ is about 5.4 inches, and the overall length is about 9 inches. In other embodiments, the dimensions of the cleaning device 500 are larger than the above mentioned dimensions (e.g., greater than 8"×12"×24"). By way of example, the dimensions of the cleaning device 500 and the size of the components disposed therein may be selected based on the intended application (e.g., based on the size of the space that the cleaning device 500 is intended to filter, etc.).

Figure 7:
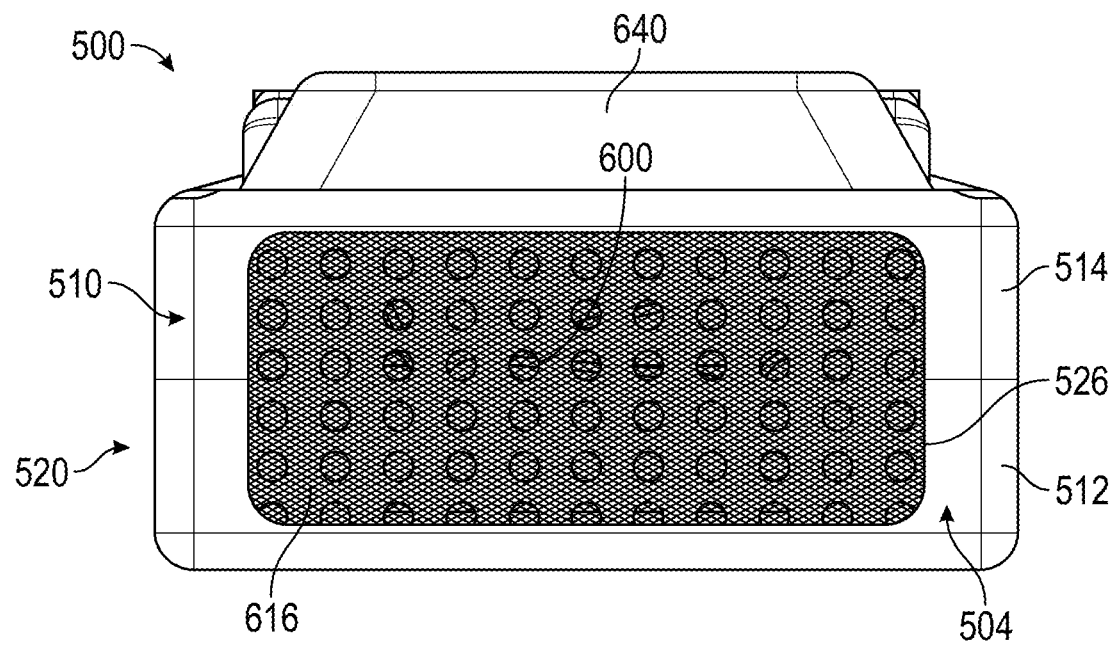
FIG. 7 is a front view of the cleaning device of FIG. 4, according to an exemplary embodiment.
Figure 8:
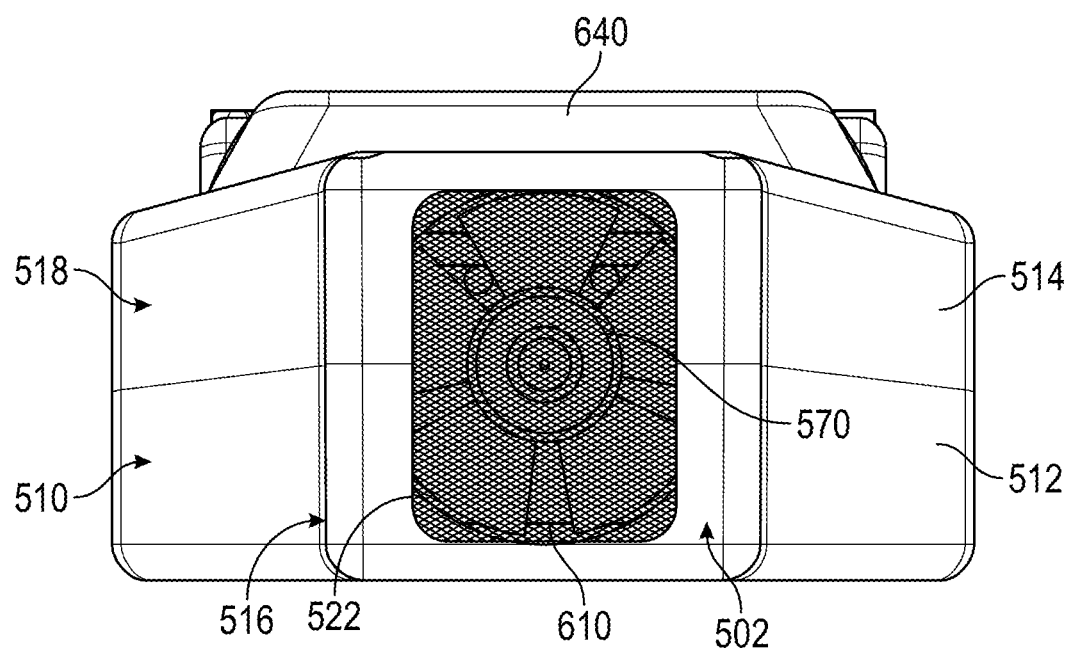
FIG. 8 is a rear view of the cleaning device of FIG. 4, according to an exemplary embodiment.
Figure 10:
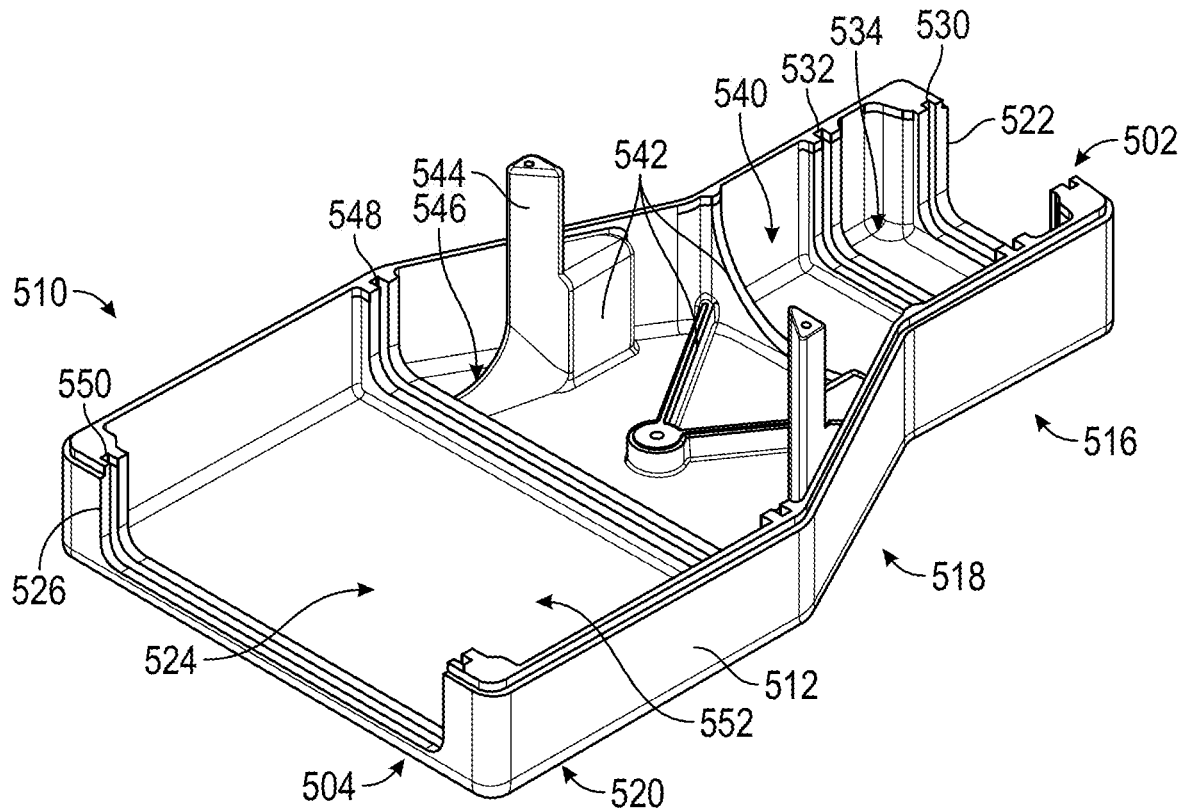
FIG. 10 is a perspective view of a bottom portion of the housing of the cleaning device of FIG. 4, according to an exemplary embodiment.
Figure 11:
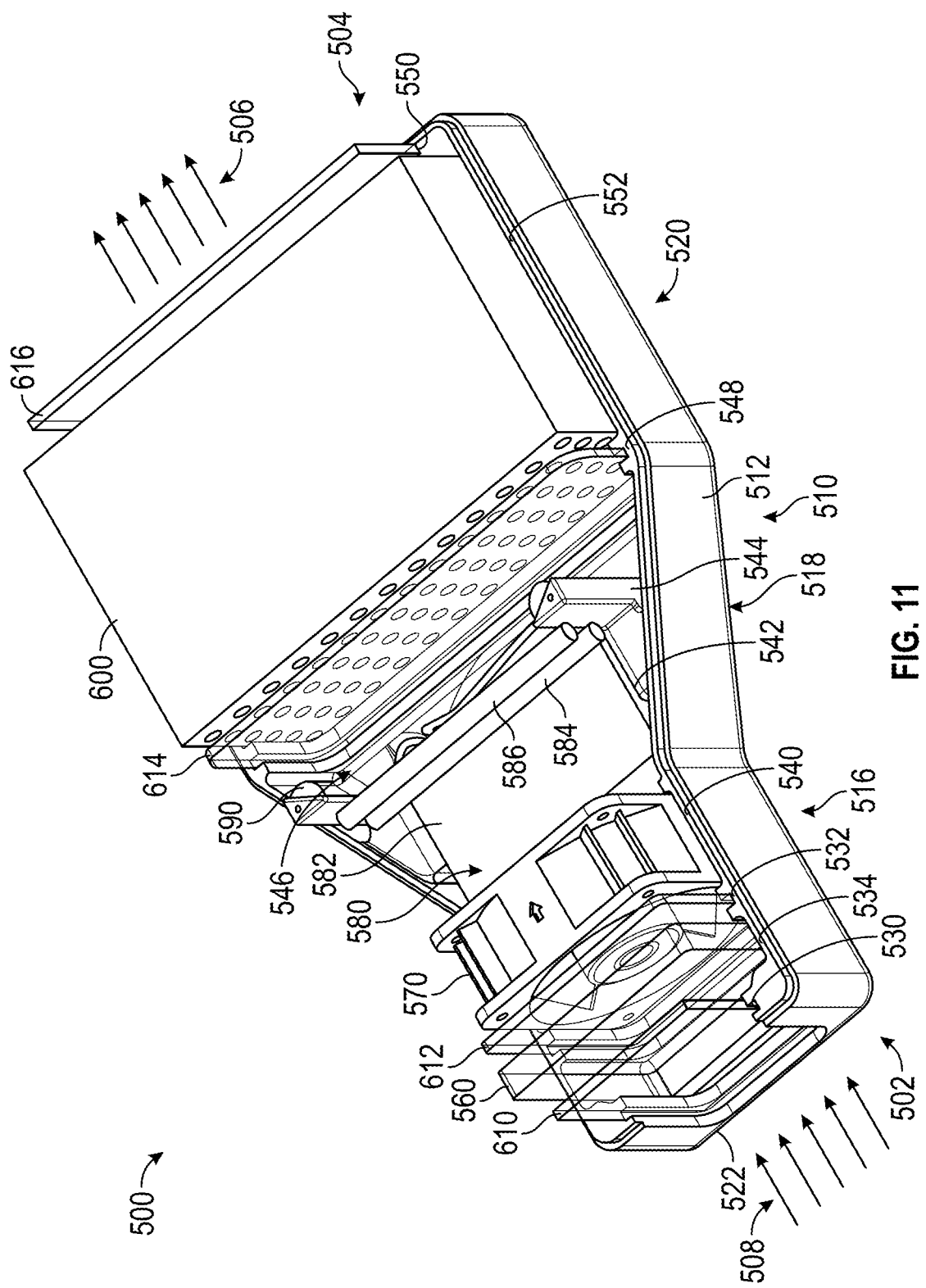
FIG. 11 is a perspective view the cleaning device of FIG. 4 with the top portion of the housing removed, according to an exemplary embodiment.
Figure 23:
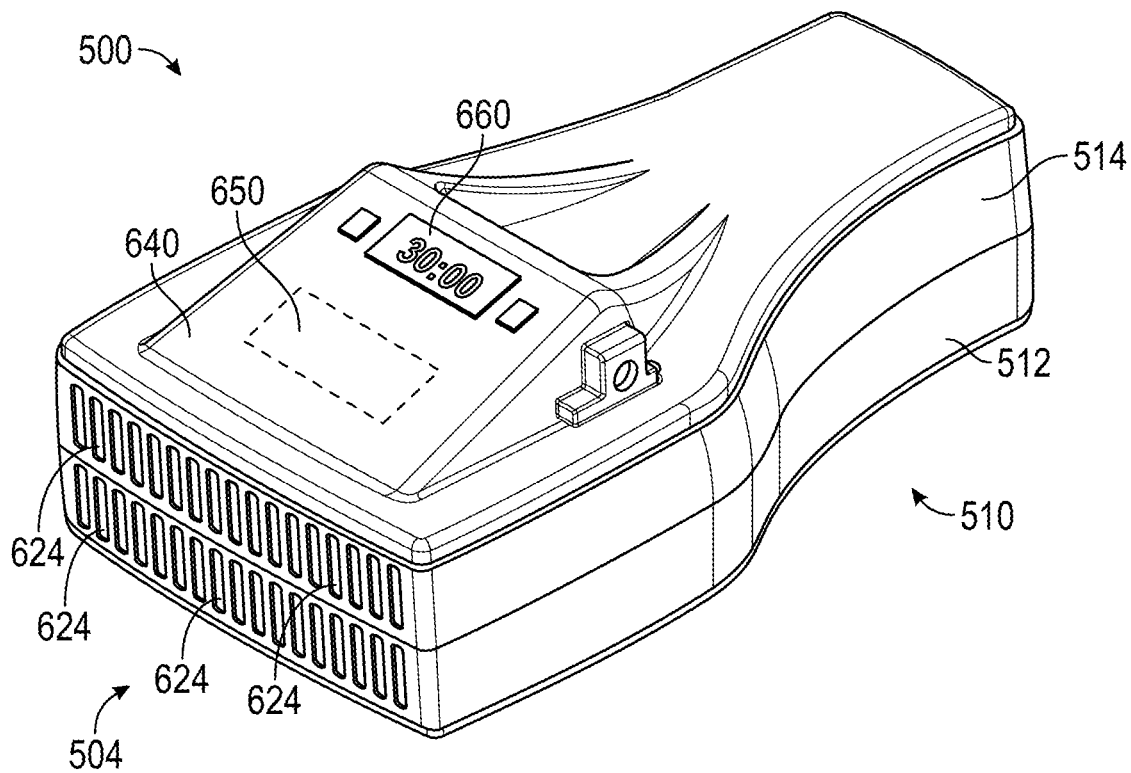
FIG. 23 is a front perspective view of a cleaning device, according to another exemplary embodiment.
Figure 24:
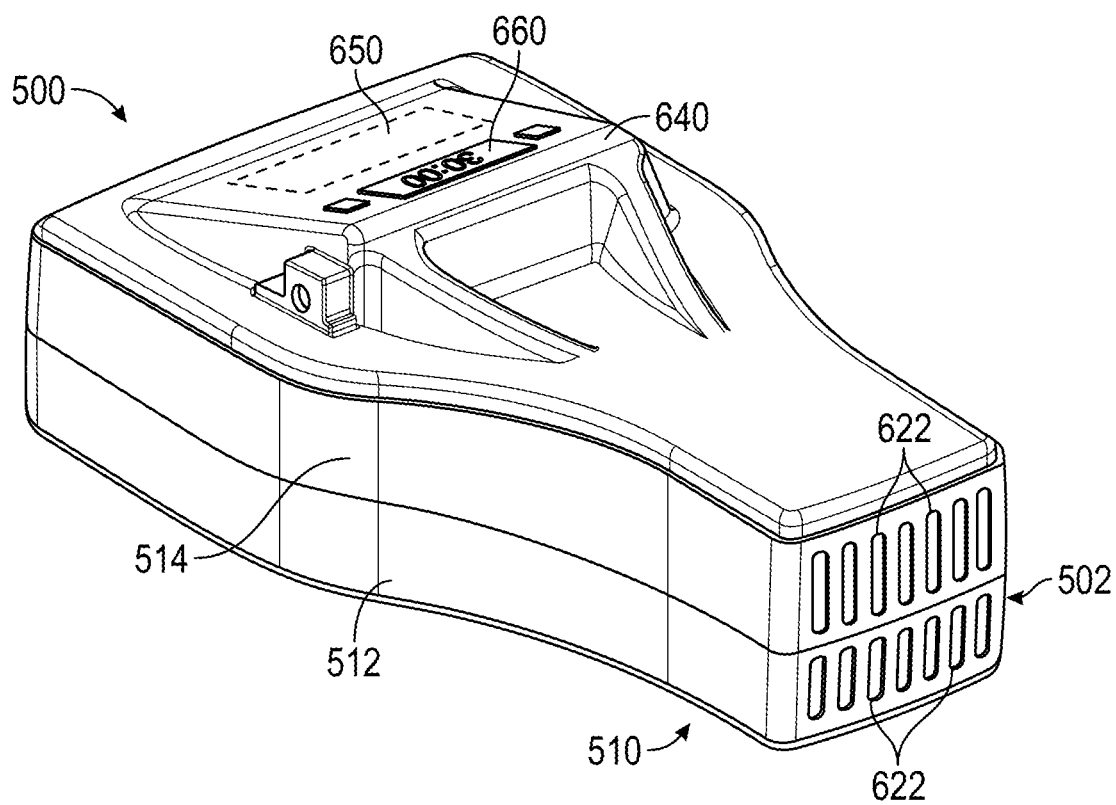
FIG. 24 is a rear perspective view of the cleaning device of FIG. 23, according to an exemplary embodiment.

As shown in FIGS. 8, 10, and 11, the base 512 and the top 514 cooperatively define a first aperture at the inlet end 502 of the housing 510, shown as inlet 522, that facilitates the flow of the contaminated air 506 into the interior cavity 524 from the external environment (e.g., the space 700, etc.). As shown in FIGS. 4, 7, and 10, the base 512 and the top 514 cooperatively define a second aperture at the outlet end 504 of the housing 510, shown as outlet 526, that facilitates the flow of the clean air 508 out of the interior cavity 524 into the external environment. Alternatively, as shown in FIGS. 23 and 24, the base 512 and the top 514 each define (i) a first plurality of apertures at the inlet end 502 of the housing 510, shown as inlets 622, that facilitate the flow of the contaminated air 506 into the interior cavity 524 from the external environment and (ii) a second plurality of apertures at the outlet end 504 of the housing 510, shown as outlets 624, that facilitate the flow of the clean air 508 out of the interior cavity 524 into the external environment.

Figure 9:
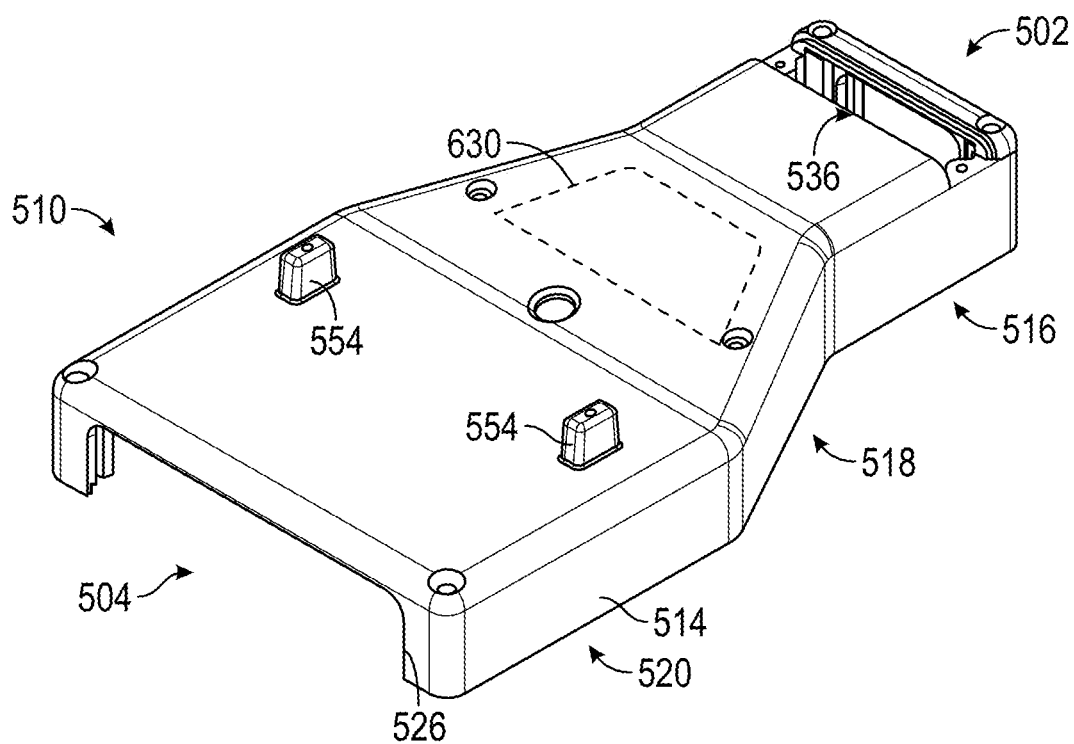
FIG. 9 is a perspective view of a top portion of a housing of the cleaning device of FIG. 4, according to an exemplary embodiment.

As shown in FIGS. 10 and 11, the inlet chamber 516 of the housing 510 defines (i) a first interface, shown as first screen slot 530, (a) positioned adjacent the inlet 522 and (b) that receives the filter inlet screen 610 such that the filter inlet screen 610 extends across the inlet 522; (ii) a second interface, shown second screen slot 532, (a) spaced from the first screen slot and (b) that receives the filter outlet screen 612; (iii) a first recess, shown as filter recess 534, (a) positioned between the first screen slot 530 and the second screen slot 532 and (b) that receives the inlet filter 560; and (iv) a second recess, shown as fan recess 540, (a) positioned on the opposite side of the second screen slot 532 relative to the filter recess 534 and (b) that receives the fan 570. As shown in FIGS. 4, 5, and 9, the top 514 of the housing 510 defines an aperture, shown as filter aperture 536, positioned to align with the filter recess 534. As shown in FIGS. 4, 5, and 14-22, the housing 510 includes a panel, shown as filter cap 538, detachably coupled to the top 514 and positioned to selectively enclose the filter aperture 536. Accordingly, the inlet filter 560 may be selectively removable (e.g., for cleaning, to be replaced, etc.) through the filter aperture 536 (i.e., without having to open the housing 510 by separating the top 514 from the bottom 512). In other embodiments, the housing 510 does not define the filter aperture 536, nor does the housing 510 include the filter cap 538 (see, e.g., FIGS. 23 and 24). The filter inlet screen 610 and the filter outlet screen 612 are configured to hold and secure the inlet filter 560 within the filter recess 534.

As shown in FIGS. 10 and 11, the ozone chamber 518 of the housing 510 includes (i) first supports, shown as ozone generator supports 542, (a) positioned adjacent the fan recess 540, (b) extending upward from the bottom 512, and (c) that support the ozone generator 580 and (ii) second supports, shown as light supports 544, (a) positioned adjacent the ozone generator supports 542, (b) extending upward from the bottom 512, and (c) that support the UV lighting 590. According to the exemplary embodiment shown in FIGS. 10 and 11, the light supports 544 are spaced a distance from the catalyst chamber 520 such that an air gap, shown as air gap 546, is positioned between the UV lighting 590 and the catalyst chamber 520.

As shown in FIGS. 10 and 11, the catalyst chamber 520 of the housing 510 defines (i) a third interface, shown as third screen slot 548, (a) positioned adjacent the air gap 546 of the ozone chamber 518 and (b) that receives the catalyst inlet screen 614; (ii) a fourth interface, shown fourth screen slot 550, (a) positioned adjacent the outlet 526 and (b) that receives the catalyst outlet screen 616 such that the catalyst outlet screen 616 extends across the outlet 526; and (iii) a third recess, shown as catalyst recess 552, (a) positioned between the third screen slot 548 and the fourth screen slot 550 and (b) that receives the catalyst 600. The catalyst inlet screen 614 and the catalyst outlet screen 616 are configured to hold and secure the catalyst 600 within the catalyst recess 552.

According to an exemplary embodiment, the fan 570 is configured to draw (e.g., pull, suck, etc.) the contaminated air 506 from the external environment into the inlet 522 and through the interior cavity 524 of the housing 510 to facilitate (i) decontaminating the contaminated air 506 with the other components of the cleaning device 500 (e.g., the inlet filter 560, the ozone generator 580, the UV lighting 590, the catalyst inlet screen 614, the catalyst 600, etc.) and (ii) emitting the clean air 508 out of the outlet 526 into the external environment. In some embodiments, the fan 570 is configured to draw the contaminated air 506 into the cleaning device 500 at a rate between 300 and 500 cubic feet per minute ("CFM") (e.g., 300 CFM, 350 CFM, 400 CFM, 450 CFM, 500 CFM, etc.). In other embodiments, the fan 570 is configured to draw in more than 500 CFM (e.g., based on the intended application of the cleaning device 500, based on the size of the fan 570, etc.). While the fan 570 is shown positioned within the inlet chamber 516 of the housing 510, proximate the inlet 522, in some embodiments, the fan 570 is otherwise positioned. By way of example, the fan 570 may be positioned within the ozone chamber 518 or within the catalyst chamber 520 (e.g., proximate the outlet 526, etc.). In some embodiments, the cleaning device 500 includes a plurality of fans 570. By way of example, a first fan 570 may be positioned proximate the inlet 522 and a second fan 570 may be positioned proximate the outlet 526. By way of another example, two or more of the fans 570 may be positioned in parallel with each other within the inlet chamber 516 and/or the catalyst chamber 520.

According to an exemplary embodiment, the inlet filter 560 is configured to filter out smoke, soot, and other particulates in the contaminated air 506 as the contaminated air 506 enters the inlet 522. In one embodiment, the inlet filter 560 is a high efficiency particular air ("HEPA") filter. The HEPA filter may be configured to remove up to 99.97% of airborne particulate matter that is 0.3 micrometers or larger in diameter. Removing such airborne particulate matter from the contaminated air 506 within a space may effectively reduce the amount of smoke, dust, and/or other particulates that would otherwise normally be recirculated by the HVAC system of the vehicle 10 and/or a building and eventually (i) settle onto surfaces within the vehicle 10 and/or the building and/or (ii) be inhaled by occupants.

According to an exemplary embodiment, the ozone generator 580 is configured to generate ozone (e.g., trioxygen, $O_3$, the ozone 588, etc.) that interacts with the contaminated air 506 to assist in the decontamination process. As shown in FIG. 11, the ozone generator 580 includes a high voltage power supply, shown as ozone power supply 582, and two spaced apart generation cells, shown as lower electrode 584 and upper electrode 586. The ozone power supply 582 of the ozone generator 580 may be powered by the power supply 670 of the cleaning device 500. The ozone power supply 582 is configured to power the lower electrode 584 and the upper electrode 586 to generate ozone. By way of example, the lower electrode 584 and the upper electrode 586 are configured to produce a cloud of electrons within the gap or "corona" therebetween. The cloud of electrons interacts with oxygen molecules as air flows therethrough, splitting the oxygen molecules into atomic oxygen. The atomic oxygen may then combine with oxygen molecules to form ozone.

According to an exemplary embodiment, the lower electrode 584 and the upper electrode 586 are positioned such that all or substantially all of the contaminated air 506 is passed through the corona of ozone generator 580 (i.e., between the lower electrode 584 and the upper electrode 586). As the contaminated air 506 passes through the corona, (i) a first portion of the contaminated air 506 (e.g., some of the oxygen in the contaminated air 506, etc.) may be converted to ozone, (ii) a second portion of the contaminated air 506 (e.g., some of the contaminates, carcinogens, pathogens, etc.) may be rendered harmless (i.e., neutralized), and/or (iii) a third portion of the contaminated air 506 may pass by unaffected. As the ozone is generated, the ozone mixes with the remaining portions of the contaminated air 506 (e.g., contaminates, carcinogens, pathogens, etc.), which may further break down the contaminates in the contaminated air 506 into harmless byproducts. In some embodiments, the cleaning device 500 does not include the ozone generator 580.

According to an exemplary embodiment, the air gap 546 is sized to provide sufficient time for the ozone to interact with the contaminated air 506 before entering the catalyst chamber 520. In some embodiments, the air gap 546 is configured to facilitate injecting moisture (e.g., humidity, water vapor, etc.) into the ozone chamber 518 to interact with the contaminated air 506 to assist in the decontamination process. The moisture may be injected through an inlet defined by the housing 510, shown as port 620 in FIGS. 4, 6, and 30, into the air gap 546 by the humidifying unit 680. The humidifying unit 680 may be an external humidifying unit that is optional.

In some embodiments, the cleaning device 500 includes an ion generator. The cleaning device 500 may include the ion generator in addition to or in place of the fan 570 and/or the ozone generator 580. By way of example, the ion generator may be configured to ionize (e.g., negatively charge, etc.) one or more molecules in the contaminated air 506. The ion generator may be configured to ionize the one or more molecules with a negative electrode (e.g., at the inlet of the ion generator, etc.). The ionized molecules may be attracted by a positive electrode at another portion (e.g., at the outlet, etc.) of the ion generator. In other embodiments, the ion generator is configured to positively charge the one or more molecules with a positive electrode, which may be attracted by a negative electrode positioned at another portion of the ion generator. The attraction of the one or more molecules to the oppositely charged electrode creates a motive force through the ion generator and the cleaning device 500. Accordingly, in some implementations, the ion generator may be configured to supplement or replace the fan 570. Further, the ion generator may be configured to produce ozone during the ionization process (e.g., which may assist in the neutralization of carcinogens, pathogens, etc.). Accordingly, in some implementations, the ion generator may be configured to supplement or replace the ozone generator 580.

According to an exemplary embodiment, the UV lighting 590 is configured to emit UV light to activate (e.g., energize, etc.) a photocatalyst. In one embodiment, the UV lighting 590 emits UV light at wavelengths between about 250 nanometers and about 455 nanometers. In some embodiments, the peak wavelength of the UV light is about 395.9 nanometers. The UV lighting 590 may include LEDs. As shown in FIGS. 22-24, the UV lighting 590 is "U-shaped." In other embodiments, the UV lighting 590 is otherwise shaped. In some embodiments, the UV lighting 590 and the catalyst inlet screen 614 are combined into a single component (i.e., not spaced from each other). In some embodiments, the cleaning device 500 does not include the UV lighting 590.

According to an exemplary embodiment, the catalyst inlet screen 614 is coated in a catalyst such that the catalyst inlet screen 614 functions as a second catalyst (i.e., in addition to the catalyst 600) that interacts with the contaminated air 506 to assist in the decontamination process. In some embodiments, the second catalyst additionally interacts with excess ozone to break the excess ozone down. In some embodiments, the coating on the catalyst inlet screen 614 is a photocatalytic coating. Accordingly, the UV lighting 590 may be configured to activate or energize the photocatalytic coating of the catalyst inlet screen 614 such that the photocatalytic coating interacts with the contaminated air 506 to assist in the decontamination process (e.g., the UV lighting 590 and the catalyst inlet screen 614 function as a photocatalytic oxidizer, etc.). By way of example, the photocatalytic coating, when irradiated with UV light in the presence of ozone, may be configured to cause rapid oxidation of contaminants (e.g., carcinogens, pathogens, etc.) that may still be present in the contaminated air 506 after passing through the inlet chamber 516 and the ozone chamber 518. In some embodiments, the photocatalytic coating includes a titanium dioxide ($TiO_2$) catalyst. In other embodiments (e.g., in embodiments where the cleaning device 500 does not include the UV lighting 590, etc.), the catalyst inlet screen 614 does not include a photocatalytic coating. In some embodiments, the catalyst inlet screen 614 does not include any type of catalyst coating and functions as a traditional screen.

Figure 12:
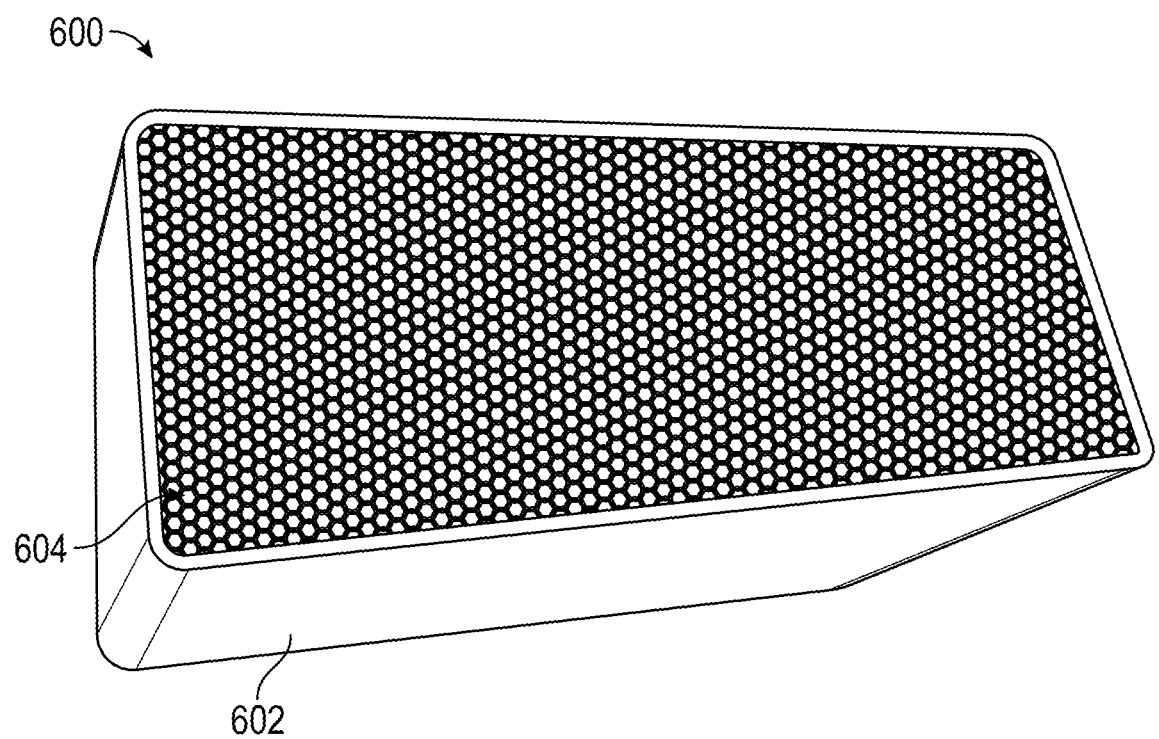
FIGS. 12 and 13 are various perspective views of a catalyst of the cleaning device of FIG. 4, according to various exemplary embodiments.
Figure 13:
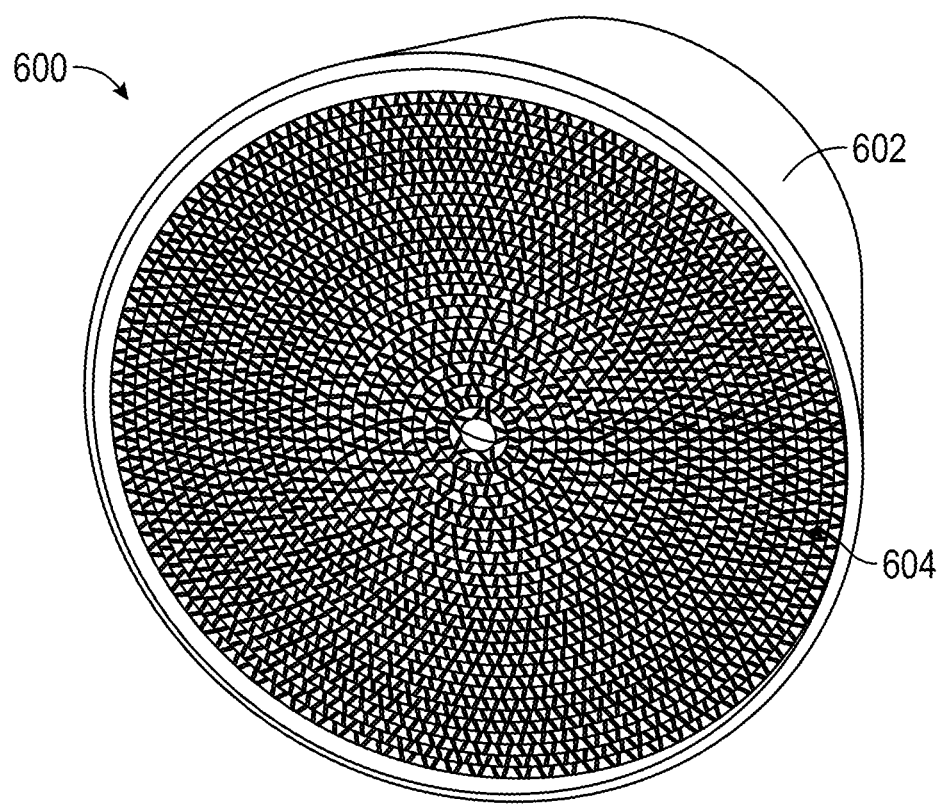
Figures 14, 15:
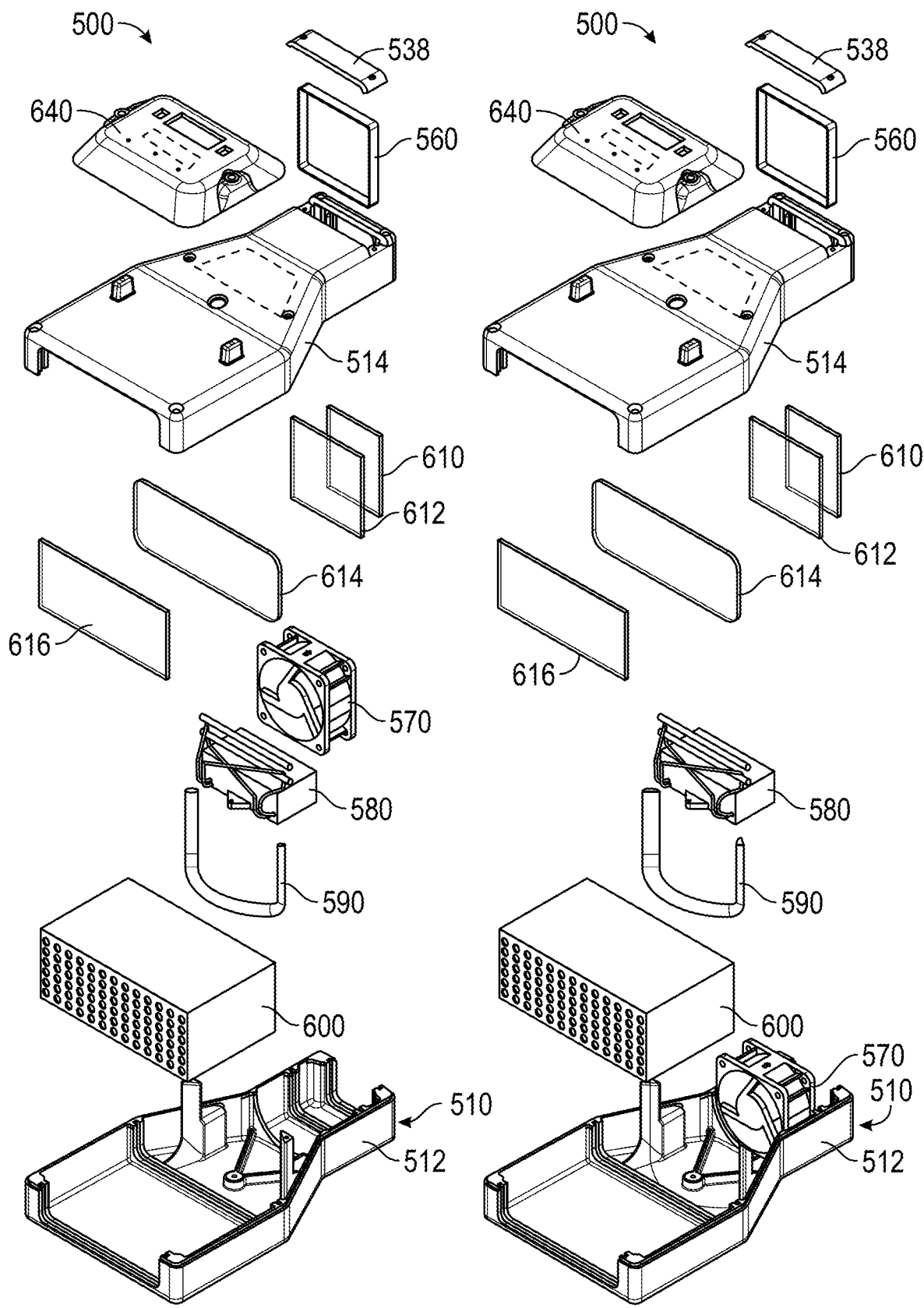
Figure 18:
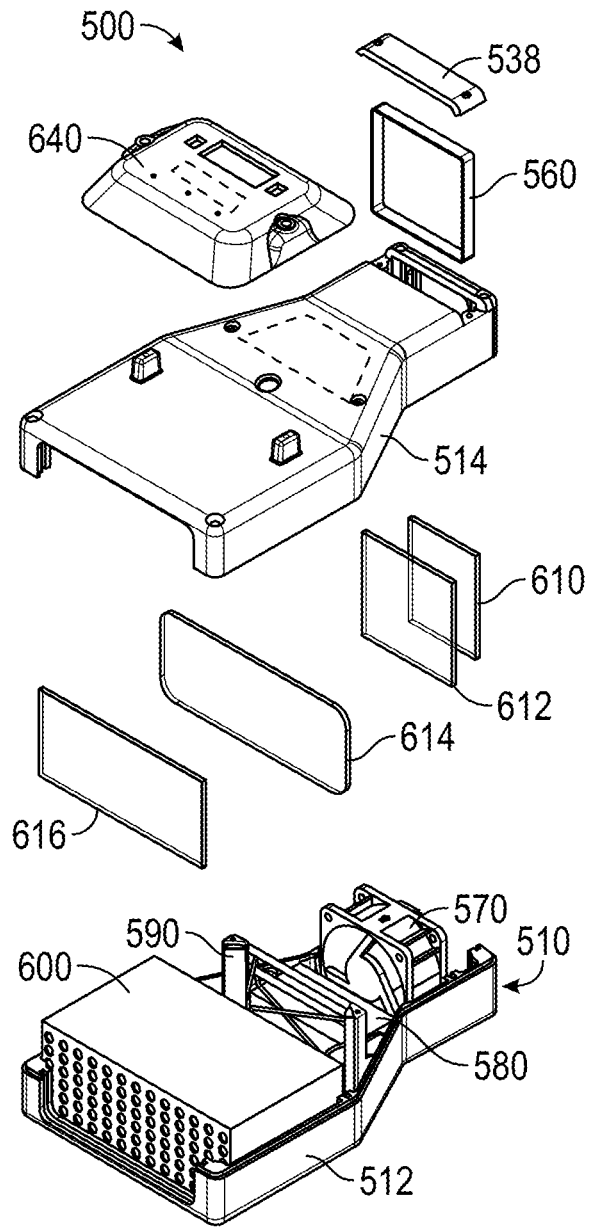
Figure 19:
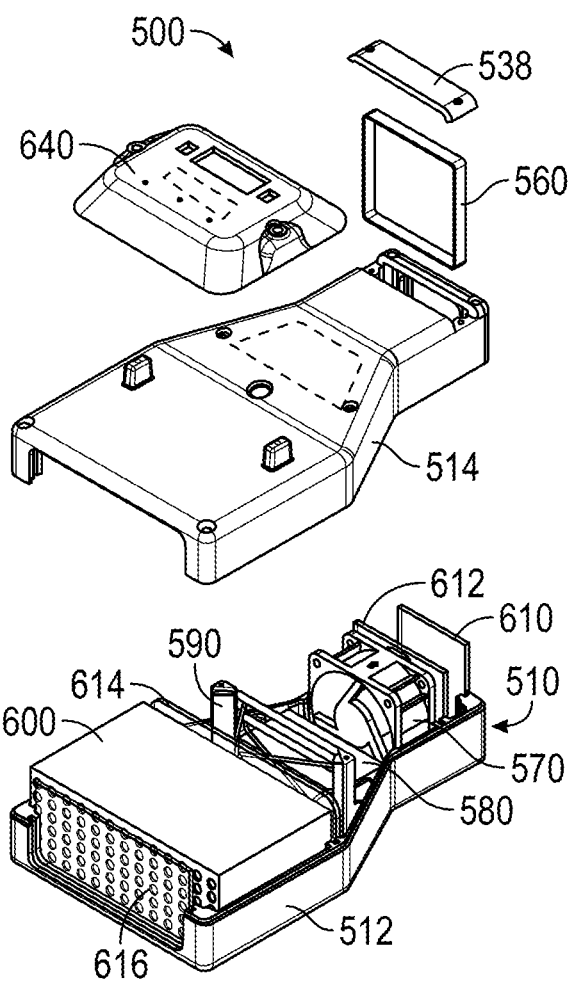

As shown in FIGS. 12 and 13, the catalyst 600 includes an outer housing, shown as catalyst housing 602, and an inner core, shown as catalyst core 604, disposed within the catalyst housing 602. As shown in FIG. 12, the catalyst housing 602 has a rectangular cross-sectional shape. As shown in FIG. 13, the catalyst housing 602 has a circular cross-sectional shape. In other embodiments, the catalyst housing 602 has another shape (e.g., based on the shape of the catalyst chamber 520, etc.). In one embodiment, the catalyst housing 602 is manufactured from a metallic material (e.g., stainless steel, etc.). In another embodiment, the catalyst housing 602 is manufactured from another type of material (e.g., plastic, ceramic, etc.).

As shown in FIGS. 12 and 13, the catalyst core 604 defines a plurality of elongated, open cells that extends through the thickness of the catalyst 600. The elongated, open cells may have a rectangular, hexagonal, circular, and/or still another cross-sectional shape. In some embodiments, the catalyst core 604 is manufactured from a metallic material, a ceramic material, and/or still another suitable material. In such embodiments, the catalyst core 604 may be coated with a catalyst coating or material that is configured to interact with the contaminated air 506 at or near room temperature (e.g., the catalyst 600 functions without requiring elevated temperatures, etc.). In some embodiments, the catalyst core 604 is manufactured from a catalyst material such that a catalyst coating is not necessary. The catalyst material may be configured to interact with the contaminated air 506 at or near room temperature. In some embodiments, the catalyst coating or the catalyst material includes manganese dioxide. In some embodiments, the catalyst coating or the catalyst material does not include manganese dioxide. In other embodiments, the catalyst 600 is configured to function at elevated temperatures. In such embodiments, the cleaning device 500 may include a heating device or heating element positioned to thermally regulate the temperature of the catalyst 600 to a target operating temperature.

According to an exemplary embodiment, the catalyst 600 is configured to receive the contaminated air 506 (or what is left of the contaminated air 506 after interacting with the ozone and the catalyst inlet screen 614) such that the catalyst coating or the catalyst material of the catalyst 600 interacts with contaminated air 506 to assist in the decontamination process. In some embodiments, the catalyst coating or the catalyst material of the catalyst 600 interacts with any remaining excess ozone to break the excess ozone down (e.g., to prevent ozone from exiting the cleaning device 500, etc.). By way of example, the catalyst 600 may be configured to neutralize the remaining ozone into individual oxygen atoms, which are themselves a much more aggressive oxidant that interact with and further reduce the contaminates in the contaminated air 506 such that clean air or cleaner air than what entered the cleaning device 500 exits the outlet 526.

In some embodiments, the cleaning device 500 does not include the ozone generator 580. In such an embodiment, the catalyst 600 may be sized such that the catalyst 600 alone is sufficient to decontaminate the contaminated air 506. In some embodiments, the cleaning device 500 includes neither the UV lighting 590 nor the photocatalytic coating on the catalyst inlet screen 614. In some embodiments, the cleaning device 500 does not include the catalyst 600. In such an embodiment, the amount of ozone produced by the ozone generator 580 may be controlled such that either all of the ozone is consumed during its interaction with the contaminated air 506 or any excess ozone is broken down via the photocatalytic coating of the catalyst inlet screen 614 and the UV light.

In some embodiments, the cleaning device 500 includes multiple stages positioned in series (e.g., two stages, three stages, etc.). In some embodiment, a first stage of the cleaning device 500 is substantially identical to a second stage of the cleaning device 500. By way of example, the first stage and the second stage may both include a fan 570, an ozone generator 580, UV lighting 590, a catalyst 600, and/or a catalyst inlet screen 614. In another embodiment, the first stage of the cleaning device 500 is different than a second stage of the cleaning device 500. By way of example, (i) the first stage may include the fan 570, the ozone generator 580, the UV lighting 590, the catalyst 600, and/or the catalyst inlet screen 614 and (ii) the second stage does not include one or more of the fan 570, the ozone generator 580, the UV lighting 590, the catalyst 600, and/or the catalyst inlet screen 614 that the first stage includes.

In some embodiments, the power supply 670 is an internal power source (e.g., a battery, a rechargeable battery, etc.) that powers the electrical components (e.g., the fan 570, the ozone generator 580, the UV lighting 590, the controller 650, etc.) of the cleaning device 500. In some embodiments, the power supply 670 is an external power source (e.g., the cleaning device 500 is hardwired to an electrical power source of a vehicle, has an electrical cord capable of being plugged into an electrical outlet, is integrated into the power grid of a building, etc.).

Figure 25:
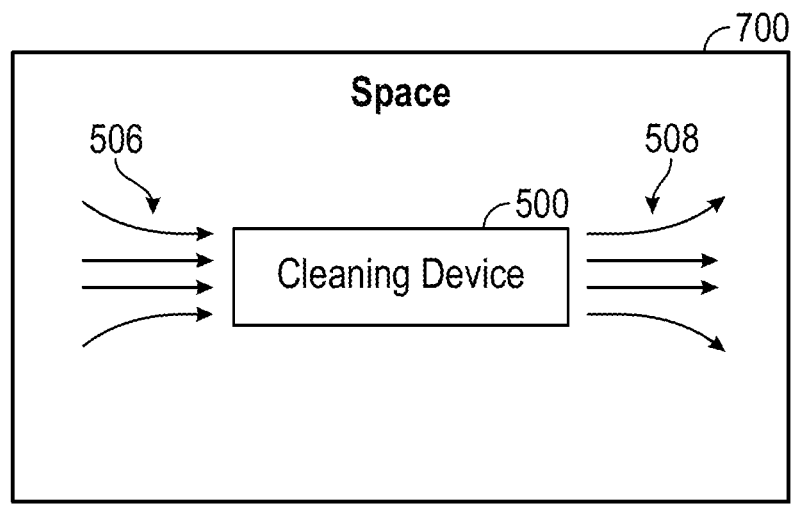
FIG. 25 is a schematic view of a cleaning device disposed within a space and operable in a first mode, according to an exemplary embodiment.

According to the exemplary embodiment shown in FIG. 25, the cleaning device 500 is configured to be disposed within a space 700 (e.g., a room, a vehicle cab, a compartment, etc.) and operable in first mode of operation or an air cycling mode of operation. During the air cycling mode of operation shown in FIG. 25, the cleaning device 500 is configured to convert the contaminated air 506 within the space 700 into the clean air 508 by (i) filtering the contaminated air 506 with the inlet filter 560, (ii) generating ozone with the ozone generator 580 to interact with the contaminated air 506, (iii) emitting UV light with the UV lighting 590 to activate the photocatalytic coating of the catalyst inlet screen 614 such that the photocatalytic coating interacts with the contaminated air 506 and/or excess ozone, (iv) providing moisture or humidity (e.g., water vapor, etc.) into the air gap 546 with the humidifying unit 680 such that the moisture interacts with the contaminated air 506 and/or excess ozone, and/or (v) passing the contaminated air through the catalyst 600 such that the catalytic coating or the catalytic material of the catalyst 600 interacts with the contaminated air and/or excess ozone such that the contaminated air 506 is converted into the clean air 508 and all or substantially all of the ozone is broken down (e.g., such that only the clean air 508 is emitted from the outlet 526, etc.). Accordingly, the cleaning device 500 can be operating while occupants are within the space 700 that the cleaning device 500 is positioned within and decontaminating (e.g., since no ozone is emitted thereby, etc.).

In some embodiments, the cleaning device 500 is configured to cycle the contaminated air 506 therethrough numerous times during the air cycling mode to provide the clean air 508. By way of example, the cleaning device 500 may be placed in a space (e.g., a cab of a vehicle, a room, etc.) that has a volume of about 350 cubic feet. If the fan 570 is configured to cycle 350 CFM through the cleaning device 500, the volume of the space 700 would be cycled through the cleaning device 500 once per minute. Accordingly, the cleaning device 500 could cycle the contaminated air 506 within the space 700 through the cleaning device 500 multiple times in a relatively short time period, each subsequent pass through removing more of the contaminates therefrom. By way of example, conservatively assuming the cleaning device 500 could remove 33% of contaminates from the contaminated air 506 in a single pass, in just twelve minutes the cleaning device 500 would remove over 98% of the contaminates within the air of the space 700.

Figure 26:
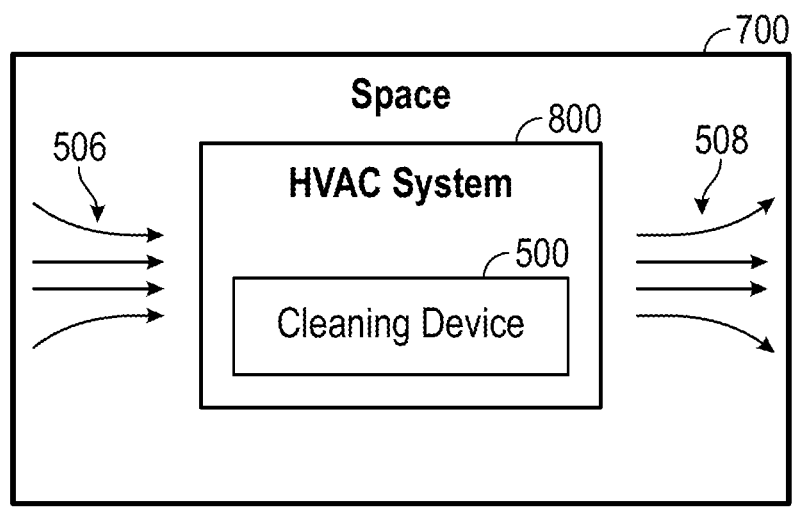
FIG. 26 is a schematic view of a cleaning device integrated into a HVAC system of a space and operable in a first mode, according to an exemplary embodiment.

According to the exemplary embodiment shown in FIG. 26, the cleaning device 500 is or various components thereof (e.g., the inlet filter 560, the ozone generator 580, the UV lighting 590, the catalyst 600, the catalyst inlet screen 614, etc.) are integrated into a ventilation system, shown as HVAC system 800, of the space 700 (e.g., along a conduit thereof, etc.) and operable in the air cycling mode of operation. In such an embodiment, one or more of the components of the cleaning device 500 described herein may not be needed. For example, the cleaning device 500 may not include the fan 570 (e.g., a fan of the HVAC system 800 may drive the air flow, etc.). During the air cycling mode of operation shown in FIG. 26, the cleaning device 500 is configured to convert the contaminated air 506 within the space 700 into the clean air 508 by (i) filtering the contaminated air 506 with the inlet filter 560 that is drawn into the HVAC system 800 (e.g., by a fan thereof, during an air recirculation mode of the HVAC system 800, etc.), (ii) generating ozone with the ozone generator 580 to interact with the contaminated air 506, (iii) emitting UV light with the UV lighting 590 to activate the photocatalytic coating of the catalyst inlet screen 614 such that the photocatalytic coating interacts with the contaminated air 506 and/or excess ozone, (iv) providing moisture or humidity (e.g., water vapor, etc.) into the air gap 546 with the humidifying unit 680 such that the moisture interacts with the contaminated air 506 and/or excess ozone, and/or (v) passing the contaminated air through the catalyst 600 such that the catalytic coating or the catalytic material of the catalyst 600 interacts with the contaminated air and/or excess ozone such that the contaminated air 506 is converted into the clean air 508 and all or substantially all of the ozone is broken down (e.g., such that only the clean air 508 is emitted from the outlet 526, etc.). The clean air 508 may then be emitted back into the space 700 by the HVAC system 800.

In some embodiments, as shown in FIGS. 27A-29B, the cleaning device 500 is additionally or alternatively operable in a second mode of operation or a flood mode of operation where the cleaning device 500 is configured to emit ozone 588 into the space 700. In some embodiments, as shown in FIGS. 4, 5, and 9, the housing 510 of the cleaning device 500 includes an openable panel, shown as flood door 630. According to an exemplary embodiment, the flood door 630 is selectively openable to facilitate operating the cleaning device 500 in the flood mode of operation. In some embodiments, the flood door 630 functions as a diverter that directs the ozone 588 out of the housing 510. By way of example, opening the flood door 630 may facilitate selectively (i) blocking off the catalyst chamber 520 (e.g., prevent ozone from passing through the catalyst 600, etc.) and/or (ii) emitting the ozone 588 from the housing 510 into the space 700 to neutralize contaminates within the space 700. In some embodiments, as shown in FIG. 30, the cleaning device 500 includes an actuator, shown as flood door actuator 632, positioned to facilitate selectively opening (e.g., during a first portion of the flood mode, etc.) and closing (e.g., during a second portion of the flood mode, during the air cycling mode, etc.) the flood door 630. In some embodiments, the cleaning device 500 includes a separate blocker element that selectively blocks the catalyst chamber 520 when the flood door 630 is open.

According to the exemplary embodiment shown in FIGS. 27A and 27B, the cleaning device 500 is configured to be disposed within the space 700 and operable in the flood mode of operation. During the flood mode of operation shown in FIGS. 27A and 27B, the cleaning device 500 is configured to neutralize contaminates within the space 700 (e.g., within the air, on surfaces, etc.) by (i) emitting the ozone 588 directly into the space 700 (e.g., through the flood door 630, etc.) such that the ozone 588 interacts with and neutralizes the contaminates within the space 700 and, thereafter, (ii) drawing the contaminated air 506 (e.g., the air containing the ozone 588, etc.) into the cleaning device 500 (e.g., with the flood door 630 closed, etc.) after a preset or selected period of time (e.g., 10, 15, 20, 25, 30, etc. minutes) to remove any excess of the ozone 588 from the space 700 (e.g., by interacting with the catalyst 600, the UV lighting 590 and the catalyst inlet screen 614, etc.).

According to the exemplary embodiment shown in FIGS. 28A and 28B, the cleaning device 500 is configured to be disposed within the space 700 and operable in the flood mode of operation in combination with the HVAC system 800. During the flood mode of operation shown in FIGS. 28A and 28B, the cleaning device 500 and the HVAC system 800 are configured to cooperatively neutralize contaminates within the space 700 (e.g., within the air, on surfaces, etc.) by (i) emitting, with the cleaning device 500, the ozone 588 directly into the space 700 (e.g., through the flood door 630, etc.) such that the ozone 588 interacts with and neutralizes the contaminates within the space 700 and, thereafter, (ii) drawing, with the HVAC system 800, the contaminated air 506 (e.g., the air containing the ozone 588, etc.) into the HVAC system 800 after a preset or selected period of time (e.g., 10, 15, 20, 25, 30, etc. minutes) and expelling the contaminated air 506 from the space 700 (e.g., using a fresh air mode of the HVAC system 800, etc.) to remove any excess of the ozone 588 from the space 700 and replacing it with fresh air from an external environment outside the space 700.

Figure 29B:
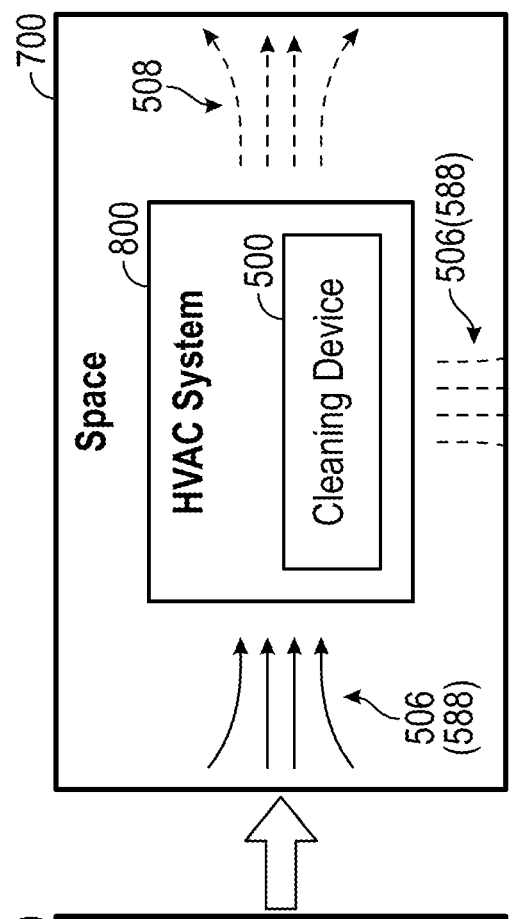
FIGS. 29A and 29B are various schematic views of a cleaning device integrated into a HVAC system of a space and operable in a second mode, according to an exemplary embodiment.
Figure 29A:
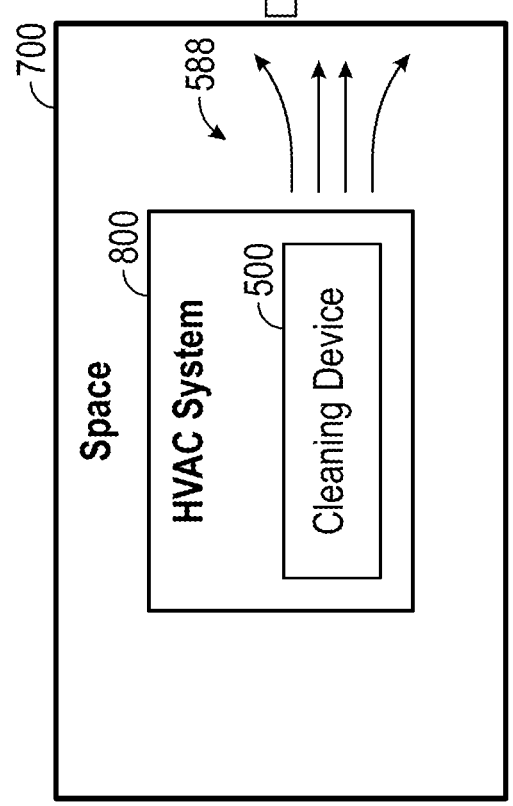

According to the exemplary embodiment shown in FIGS. 29A and 29B, the cleaning device 500 is or various components thereof are integrated into the HVAC system 800 of the space 700 (e.g., along a conduit thereof, etc.) and operable in the flood mode of operation. In such an embodiment, one or more of the components of the cleaning device 500 described herein may not be needed. For example, the cleaning device 500 may not include the fan 570 (e.g., a fan of the HVAC system 800 may drive the air flow, etc.). During the flood mode of operation shown in FIGS. 29A and 29B, the cleaning device 500 and the HVAC system 800 are configured to cooperatively neutralize contaminates within the space 700 (e.g., within the air, on surfaces, etc.) by (i) the emitting, with the cleaning device 500 through the HVAC system 800 (e.g., conduits thereof, etc.), the ozone 588 directly into the space 700 such that the ozone 588 interacts with and neutralizes the contaminates within the space 700 and, thereafter, (ii) drawing, with the HVAC system 800, the contaminated air 506 (e.g., the air containing the ozone 588, etc.) into the HVAC system 800 after a preset or selected period of time (e.g., 10, 15, 20, 25, 30, etc. minutes). In some embodiments, the HVAC system 800 is configured to expel the contaminated air 506 from the space 700 (e.g., using a fresh air mode of the HVAC system 800, etc.) to remove any excess of the ozone 588 from the space 700 and replace it with fresh air from an external environment outside the space 700. In some embodiments, the HVAC system 800 is configured to draw the contaminated air 506 into the cleaning device 500 for treatment (i.e., neutralize the ozone 588) to produce the clean air 508 and, then, the HVAC system 800 is configured to emit the clean air 508 into the space 700.

As shown in FIG. 9, the top 514 of the housing 510 includes an interface, shown as controller interface 554. According to an exemplary embodiment, the controller interface 554 is configured to engage with and secure the controller housing 640 to the top 514 of the housing 510. In other embodiments, as shown in FIGS. 23 and 24, the controller housing 640 is integrally formed with the top 514 of the housing 510. As shown in FIGS. 4, 5, 23, and 24, the controller housing 640 receives the controller 650 and the user interface 660 is disposed along the exterior of the controller housing 640. According to an exemplary embodiment, the controller 650 is configured to selectively engage, selectively disengage, control, and/or otherwise communicate with components of the cleaning device 500. As shown in FIG. 30, the controller 650 is configured to selectively engage, selectively disengage, control, and/or otherwise communicate with the fan 570, the ozone generator 580, the UV lighting 590, the flood door actuator 632, the user interface 660, the power supply 670, and/or the humidifying unit 680.

In some embodiments, the controller 650 is configured to communicate with systems of the space 700 (e.g., vehicle systems, building systems, the HVAC system 800, etc.). By way of example, the controller 650 may be configured to send a signal to a control system of the space 700 to lock the doors thereto during the flood mode of operation of the cleaning device 500 (e.g., the prevent people from entering the space 700 until the decontamination process is completed and the ozone 588 is neutralized, etc.). By way of another example, the controller 650 may be configured to automatically cease emitting the ozone 588 into the space 700 if the doors thereto are opened. In some implementations, the controller 650 may be configured to switch operation of the cleaning device 500 from the flood mode to the air cycling mode in response to the door being opened (e.g., to remove any of the ozone 588 from the space 700, etc.).

According to an exemplary embodiment, the user interface 660 is configured to facilitate (i) providing inputs (e.g., commands, etc.) to the controller 650 and/or (ii) providing outputs (e.g., feedback, status information, etc.) to an operator of the cleaning device 500. The user interface 660 may include a display screen configured to provide a graphical user interface ("GIU") to an operator thereof. The user interface 660 may additionally or alternatively include various control features such as touch screen, buttons, switches, dials, etc. An operator may provide commands to the controller 650 with the user interface 660 such as an indication of a desired decontamination time, a selection of a predefined decontamination mode (e.g., the flood mode, the air cycling mode, etc.), a command to start and/or stop a decontamination cycle, etc. The controller 650 may be configured to provide feedback to the operator with the user interface 660 such as an indication of a remaining time left in a decontamination cycle, an indication when the decontamination cycle is completed (e.g., visual, audible, etc.), an indication that the inlet filter 560 should be changed or cleaned, an indication that the catalyst 600 is spent, and/or still other alerts or notifications.

The controller 650 may be implemented as a general-purpose processor, an application specific integrated circuit (ASIC), one or more field programmable gate arrays (FPGAs), a digital-signal-processor (DSP), circuits containing one or more processing components, circuitry for supporting a microprocessor, a group of processing components, or other suitable electronic processing components. According to the exemplary embodiment shown in FIG. 30, the controller 650 includes a processing circuit 652 having a processor 654 and a memory 656. The processing circuit 652 may include an ASIC, one or more FPGAs, a DSP, circuits containing one or more processing components, circuitry for supporting a microprocessor, a group of processing components, or other suitable electronic processing components. In some embodiments, the processor 654 is configured to execute computer code stored in the memory 656 to facilitate the activities described herein. The memory 656 may be any volatile or non-volatile computer-readable storage medium capable of storing data or computer code relating to the activities described herein. According to an exemplary embodiment, the memory 656 includes computer code modules (e.g., executable code, object code, source code, script code, machine code, etc.) configured for execution by the processor 654.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

The hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device) may include one or more devices (e.g., RAM, ROM, Flash memory, hard disk storage) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It is important to note that the construction and arrangement of the cleaning device 500 as shown in the various exemplary embodiments is illustrative only. Additionally, any element disclosed in one embodiment may be incorporated or utilized with any other embodiment disclosed herein. Although only one example of an element from one embodiment that can be incorporated or utilized in another embodiment has been described above, it should be appreciated that other elements of the various embodiments may be incorporated or utilized with any of the other embodiments disclosed herein.

The invention claimed is:

1. A cleaning device comprising:
a housing defining an inlet, an outlet, and an internal cavity connecting the inlet to the outlet, wherein the housing includes a door that is selectively openable;
an ozone generator positioned within the internal cavity;
a catalyst positioned within the internal cavity; and
an air driver positioned within the internal cavity, the air driver configured to draw contaminated air from an external environment into the inlet, across the ozone generator, and through the catalyst to facilitate decontaminating the contaminated air and emitting clean air out of the outlet into the external environment;
wherein the ozone generator is configured to convert at least a portion of oxygen within the contaminated air into ozone as the contaminated air flows across the ozone generator;
wherein at least one of the ozone or the catalyst is configured to interact with the contaminated air to produce the clean air; and
wherein the cleaning device is operable in (i) a first mode where the door is closed such that the contaminated air is cycled through the housing and the clean air is emitted from the outlet of the housing and (ii) a second mode where the door is open and the ozone is emitted from the housing through the door into the external environment such that the ozone bypasses the catalyst and the outlet.

2. The cleaning device of claim 1, wherein the housing includes a port configured to interface with a humidifying unit to facilitate injecting moisture into the internal cavity.

3. The cleaning device of claim 1, wherein the air driver includes a fan.

4. The cleaning device of claim 1, wherein the air driver includes an ion generator.

5. The cleaning device of claim 1, wherein the housing has an inlet chamber that defines the inlet and an outlet chamber that defines the outlet, wherein the inlet chamber has a first width and the outlet chamber has a second width that is different than the first width.

6. The cleaning device of claim 5, wherein the first width is at most eight inches and the second width is at most twelve inches, and wherein the housing has an overall length of at most twenty-four inches.

7. The cleaning device of claim 5, wherein the housing has an intermediate chamber connecting the inlet chamber and the outlet chamber, wherein the intermediate chamber has at least one of a linear profile or a non-linear profile.

8. The cleaning device of claim 1, wherein the air driver is positioned upstream of the ozone generator and the catalyst.

9. The cleaning device of claim 1, wherein the air driver is positioned downstream of at least one of the ozone generator or the catalyst.

10. The cleaning device of claim 1, wherein the catalyst is a first catalyst, further comprising:
a first screen positioned upstream of the first catalyst, wherein the first screen is coated with a catalyst material such that the first screen comprises a second catalyst; and
a second screen positioned downstream of the first catalyst such that the first catalyst is positioned between the first screen and the second screen.

11. The cleaning device of claim 10, wherein the first catalyst is positioned to neutralize excess ozone that does not interact with the contaminated air such that the excess ozone does not exit the outlet of the housing.

12. The cleaning device of claim 10, further comprising a filter positioned within the internal cavity, proximate the inlet.

13. The cleaning device of claim 12, further comprising a third screen positioned upstream of the filter and a fourth screen positioned downstream of the filter such that the filter is positioned between the third screen and the fourth screen, wherein the third screen and the fourth screen assist in holding the filter in place.

14. The cleaning device of claim 12, wherein the housing defines a filter aperture and includes a cap positioned to selectively enclose the filter aperture, and wherein the cap is selectively removable to facilitate removing the filter from the internal cavity through the filter aperture.

15. The cleaning device of claim 10, further comprising an ultraviolet light source positioned within the internal cavity and configured to emit ultraviolet light.

16. The cleaning device of claim 15, wherein the ultraviolet light source is positioned between the ozone generator and the first catalyst.

17. The cleaning device of claim 15, wherein the catalyst material of the first screen is a photocatalyst material, and wherein the first screen and the ultraviolet light source function as a photocatalytic oxidizer.

18. The cleaning device of claim 17, wherein the first screen is spaced from the ultraviolet light source such that a gap is formed therebetween.

19. The cleaning device of claim 17, wherein the first screen and the ultraviolet light source are integrated into a single component.

20. The cleaning device of claim 10, wherein the first screen and the second screen assist in holding the first catalyst in place.

* * * * *